(12) United States Patent
Beidler et al.

(10) Patent No.: US 7,723,484 B2
(45) Date of Patent: May 25, 2010

(54) ANTI-EGFR ANTIBODIES

(75) Inventors: Catherine Brautigam Beidler, Poway, CA (US); Alain Philippe Vasserot, Carlsbad, CA (US); Jeffry Dean Watkins, Encinitas, CA (US)

(73) Assignee: Applied Molecular Evolution, Inc., San Diego, CA (US)

( * ) Notice: Subject to any disclaimer, the term of this patent is extended or adjusted under 35 U.S.C. 154(b) by 157 days.

(21) Appl. No.: 12/090,395

(22) PCT Filed: Nov. 6, 2006

(86) PCT No.: PCT/US2006/043311

§ 371 (c)(1), (2), (4) Date: Apr. 16, 2008

(87) PCT Pub. No.: WO2007/058823

PCT Pub. Date: May 24, 2007

(65) Prior Publication Data

US 2008/0274114 A1    Nov. 6, 2008

Related U.S. Application Data

(60) Provisional application No. 60/735,363, filed on Nov. 12, 2005.

(51) Int. Cl.
*C07K 14/52* (2006.01)

(52) U.S. Cl. ............................. 530/387.1; 424/130.1

(58) Field of Classification Search ........................ None
See application file for complete search history.

(56) References Cited

FOREIGN PATENT DOCUMENTS

| | | | |
|---|---|---|---|
| EP | 1 500 329 A | 1/2005 | |
| WO | WO 96/40210 A | 12/1996 | |
| WO | WO 98/50433 A | 11/1998 | |
| WO | WO 2005/010151 A | 2/2005 | |

OTHER PUBLICATIONS

Baselfa J., et al., *Journal of Clinical Oncology*, "Critical Update and Emerging Trends in Epidermal Growth Factor Receptor Targeting in Cancer", vol. 23 (2005) pp. 2445-2459.

Yang, X-D, et al., *Critical Reviews in Oncology/Hematology*, "Development of ABX-EGF, a fully human anti-EGF receptor monoclonal antibody, for cancer therapy", vol. 38 (2001) pp. 17-23.

Vanhoefer, U. et al., *Journal of Clinical Oncology*, "Phase I Study of the Humanized Antiepidermal Growth Factor Receptor Monoclonal antibody EMD72000 in Patients With Advanced Solid Tumors That Express the Epidermal Growth Factor Receptor", vol. 22 (2004) pp. 175-184.

Crombet T., et al., *Journal of Clinical Oncology*, "Use of the Humanized Anti-Epidermal Growth Factor Receptor Monoclonal Antibody h-R3 in Combination With Radiotherapy in the Treatment of Locally Advance Head and Neck Cancer Patients", vol. 22 (2004) pp. 1646-1654.

Herbst R., et al., *Seminars in Oncology*, "Epidermal Growth Factor Receptors as a Target for Cancer Treatment: The Emerging Role of IMC-C225 in the Treatment of Lung and Head and Neck Cancers", vol. 29 (2002) pp. 27-36.

*Primary Examiner*—Larry R. Helms
*Assistant Examiner*—Meera Natarajan
(74) *Attorney, Agent, or Firm*—Averie K. Hason; Robert L. Sharp

(57) ABSTRACT

The present invention encompasses EGFR specific monoclonal antibodies, or antigen-binding portions thereof. These antibodies, or antigen-binding portions thereof, have high affinity for EGFR, inhibit the activation of EGFR, and are useful for the treatment of EGFR mediated cancers.

4 Claims, 7 Drawing Sheets

Inhibition of receptor phosphorylation correlates with potency in cell-based assay.

Established A431 Tumors treated with multiple doses of antibody.

```
                          SEQUENCE LISTING

<160> NUMBER OF SEQ ID NOS: 82

<210> SEQ ID NO 1
<211> LENGTH: 10
<212> TYPE: PRT
<213> ORGANISM: Artificial
<220> FEATURE:
<223> OTHER INFORMATION: Synthetic construct

<400> SEQUENCE: 1

Gly Phe Ser Leu Thr Asn Tyr Gly Val His
1               5                   10

<210> SEQ ID NO 2
<211> LENGTH: 10
<212> TYPE: PRT
<213> ORGANISM: Artificial
<220> FEATURE:
<223> OTHER INFORMATION: Synthetic construct

<400> SEQUENCE: 2

Gly Phe Ser Leu Thr Asn Trp Gly Val His
1               5                   10

<210> SEQ ID NO 3
<211> LENGTH: 10
<212> TYPE: PRT
<213> ORGANISM: Artificial
<220> FEATURE:
<223> OTHER INFORMATION: Synthetic construct

<400> SEQUENCE: 3

Gly Phe Ser Leu Thr Asn Tyr Asp Val His
1               5                   10

<210> SEQ ID NO 4
<211> LENGTH: 10
<212> TYPE: PRT
<213> ORGANISM: Artificial
<220> FEATURE:
<223> OTHER INFORMATION: Synthetic construct

<400> SEQUENCE: 4

Gly Phe Ser Leu Thr Asn Tyr Glu Val His
1               5                   10

<210> SEQ ID NO 5
<211> LENGTH: 10
<212> TYPE: PRT
<213> ORGANISM: Artificial
<220> FEATURE:
<223> OTHER INFORMATION: Synthetic construct

<400> SEQUENCE: 5

Gly Phe Ser Leu Thr Asn Tyr Ala Val His
1               5                   10

<210> SEQ ID NO 6
<211> LENGTH: 10
```

```
<212> TYPE: PRT
<213> ORGANISM: Artificial
<220> FEATURE:
<223> OTHER INFORMATION: Synthetic construct

<400> SEQUENCE: 6

Gly Phe Ser Leu Ser Asn Trp Gly Val His
1               5                   10

<210> SEQ ID NO 7
<211> LENGTH: 10
<212> TYPE: PRT
<213> ORGANISM: Artificial
<220> FEATURE:
<223> OTHER INFORMATION: Synthetic construct

<400> SEQUENCE: 7

Gly Phe Ser Leu Ser Asn Trp Glu Val His
1               5                   10

<210> SEQ ID NO 8
<211> LENGTH: 10
<212> TYPE: PRT
<213> ORGANISM: Artificial
<220> FEATURE:
<223> OTHER INFORMATION: Synthetic construct

<400> SEQUENCE: 8

Gly Phe Ser Leu Ser Asn Trp Ala Val His
1               5                   10

<210> SEQ ID NO 9
<211> LENGTH: 10
<212> TYPE: PRT
<213> ORGANISM: Artificial
<220> FEATURE:
<223> OTHER INFORMATION: Synthetic construct

<400> SEQUENCE: 9

Gly Phe Ser Leu Ser Asn Trp Asp Val His
1               5                   10

<210> SEQ ID NO 10
<211> LENGTH: 10
<212> TYPE: PRT
<213> ORGANISM: Artificial
<220> FEATURE:
<223> OTHER INFORMATION: Synthetic construct

<400> SEQUENCE: 10

Gly Phe Ser Leu Thr Asn Trp Asp Val His
1               5                   10

<210> SEQ ID NO 11
<211> LENGTH: 16
<212> TYPE: PRT
<213> ORGANISM: Artificial
<220> FEATURE:
<223> OTHER INFORMATION: Synthetic construct

<400> SEQUENCE: 11

Val Ile Trp Ser Gly Gly Asn Thr Asp Tyr Asn Thr Pro Phe Thr Ser
1               5                   10                  15

<210> SEQ ID NO 12
<211> LENGTH: 16
<212> TYPE: PRT
```

```
<213> ORGANISM: Artificial
<220> FEATURE:
<223> OTHER INFORMATION: Synthetic construct

<400> SEQUENCE: 12

Val Ile Trp Ser Gly Gly Ala Thr Asp Tyr Asn Thr Pro Phe Thr Ser
1               5                   10                  15

<210> SEQ ID NO 13
<211> LENGTH: 16
<212> TYPE: PRT
<213> ORGANISM: Artificial
<220> FEATURE:
<223> OTHER INFORMATION: Synthetic construct

<400> SEQUENCE: 13

Val Ile Trp Ser Gly Gly Ser Thr Asp Tyr Asn Thr Pro Phe Thr Ser
1               5                   10                  15

<210> SEQ ID NO 14
<211> LENGTH: 16
<212> TYPE: PRT
<213> ORGANISM: Artificial
<220> FEATURE:
<223> OTHER INFORMATION: Synthetic construct

<400> SEQUENCE: 14

Val Ile Trp Ser Gly Gly Asn Asp Asp Tyr Asn Thr Pro Phe Asp Ser
1               5                   10                  15

<210> SEQ ID NO 15
<211> LENGTH: 16
<212> TYPE: PRT
<213> ORGANISM: Artificial
<220> FEATURE:
<223> OTHER INFORMATION: Synthetic construct

<400> SEQUENCE: 15

Val Ile Trp Ser Gly Gly Ala Thr Asp Tyr Asn Thr Pro Phe Asp Ser
1               5                   10                  15

<210> SEQ ID NO 16
<211> LENGTH: 16
<212> TYPE: PRT
<213> ORGANISM: Artificial
<220> FEATURE:
<223> OTHER INFORMATION: Synthetic construct

<400> SEQUENCE: 16

Val Ile Trp Ser Gly Gly Asn Thr Asp Tyr Asn Thr Pro Phe Ala Ser
1               5                   10                  15

<210> SEQ ID NO 17
<211> LENGTH: 16
<212> TYPE: PRT
<213> ORGANISM: Artificial
<220> FEATURE:
<223> OTHER INFORMATION: Synthetic construct

<400> SEQUENCE: 17

Val Ile Trp Ser Gly Gly Ala Thr Asp Tyr Asn Thr Pro Phe Asn Ser
1               5                   10                  15

<210> SEQ ID NO 18
<211> LENGTH: 16
<212> TYPE: PRT
<213> ORGANISM: Artificial
```

```
<220> FEATURE:
<223> OTHER INFORMATION: Synthetic construct

<400> SEQUENCE: 18

Asn Ile Trp Ser Gly Gly Asn Thr Asp Tyr Asn Thr Pro Phe Thr Ser
1               5                   10                  15

<210> SEQ ID NO 19
<211> LENGTH: 16
<212> TYPE: PRT
<213> ORGANISM: Artificial
<220> FEATURE:
<223> OTHER INFORMATION: Synthetic construct

<400> SEQUENCE: 19

Val Ile Trp Ser Gly Gly Thr Thr Asp Tyr Asn Thr Pro Phe Thr Ser
1               5                   10                  15

<210> SEQ ID NO 20
<211> LENGTH: 16
<212> TYPE: PRT
<213> ORGANISM: Artificial
<220> FEATURE:
<223> OTHER INFORMATION: Synthetic construct

<400> SEQUENCE: 20

Val Ile Trp Ser Gly Gly Asn Pro Asp Tyr Asn Thr Pro Phe Thr Ser
1               5                   10                  15

<210> SEQ ID NO 21
<211> LENGTH: 16
<212> TYPE: PRT
<213> ORGANISM: Artificial
<220> FEATURE:
<223> OTHER INFORMATION: Synthetic construct

<400> SEQUENCE: 21

Asn Ile Trp Ser Gly Gly Thr Pro Asp Tyr Asn Thr Pro Phe Thr Ser
1               5                   10                  15

<210> SEQ ID NO 22
<211> LENGTH: 16
<212> TYPE: PRT
<213> ORGANISM: Artificial
<220> FEATURE:
<223> OTHER INFORMATION: Synthetic construct

<400> SEQUENCE: 22

Asn Ile Trp Ser Gly Gly Ala Pro Asp Tyr Asn Thr Pro Phe Thr Ser
1               5                   10                  15

<210> SEQ ID NO 23
<211> LENGTH: 16
<212> TYPE: PRT
<213> ORGANISM: Artificial
<220> FEATURE:
<223> OTHER INFORMATION: Synthetic construct

<400> SEQUENCE: 23

Asn Ile Trp Ser Gly Gly Asn Pro Asp Tyr Asn Thr Pro Phe Thr Ser
1               5                   10                  15

<210> SEQ ID NO 24
<211> LENGTH: 12
<212> TYPE: PRT
<213> ORGANISM: Artificial
<220> FEATURE:
```

-continued

<223> OTHER INFORMATION: Synthetic construct

<400> SEQUENCE: 24

Gly Phe Ser Leu Arg Lys Val Gly Arg Ser Val Ser
1               5                   10

<210> SEQ ID NO 25
<211> LENGTH: 11
<212> TYPE: PRT
<213> ORGANISM: Artificial
<220> FEATURE:
<223> OTHER INFORMATION: Synthetic construct

<400> SEQUENCE: 25

Ala Leu Asp Tyr Tyr Asp Tyr Glu Phe Ala Tyr
1               5                   10

<210> SEQ ID NO 26
<211> LENGTH: 11
<212> TYPE: PRT
<213> ORGANISM: Artificial
<220> FEATURE:
<223> OTHER INFORMATION: Synthetic construct

<400> SEQUENCE: 26

Ala Leu Asp Tyr Tyr Asp Tyr Asn Phe Ala Tyr
1               5                   10

<210> SEQ ID NO 27
<211> LENGTH: 11
<212> TYPE: PRT
<213> ORGANISM: Artificial
<220> FEATURE:
<223> OTHER INFORMATION: Synthetic construct

<400> SEQUENCE: 27

Ala Leu Asp Tyr Tyr Asp Tyr Asp Phe Ala Tyr
1               5                   10

<210> SEQ ID NO 28
<211> LENGTH: 11
<212> TYPE: PRT
<213> ORGANISM: Artificial
<220> FEATURE:
<223> OTHER INFORMATION: Synthetic construct

<400> SEQUENCE: 28

Ala Leu Asp Tyr Tyr Asp Tyr Glu Tyr Ala Tyr
1               5                   10

<210> SEQ ID NO 29
<211> LENGTH: 11
<212> TYPE: PRT
<213> ORGANISM: Artificial
<220> FEATURE:
<223> OTHER INFORMATION: Synthetic construct

<400> SEQUENCE: 29

Ala Leu Asp Tyr Tyr Asp Tyr Asp Tyr Ala Tyr
1               5                   10

<210> SEQ ID NO 30
<211> LENGTH: 11
<212> TYPE: PRT
<213> ORGANISM: Artificial
<220> FEATURE:
<223> OTHER INFORMATION: Synthetic construct

```
<400> SEQUENCE: 30

Arg Ala Ser Gln Ser Ile Gly Thr Asn Ile His
1               5                   10

<210> SEQ ID NO 31
<211> LENGTH: 11
<212> TYPE: PRT
<213> ORGANISM: Artificial
<220> FEATURE:
<223> OTHER INFORMATION: Synthetic construct

<400> SEQUENCE: 31

Arg Ala Ser Glu Ser Ile Gly Thr Asn Ile His
1               5                   10

<210> SEQ ID NO 32
<211> LENGTH: 11
<212> TYPE: PRT
<213> ORGANISM: Artificial
<220> FEATURE:
<223> OTHER INFORMATION: Synthetic construct

<400> SEQUENCE: 32

Arg Ala Ser Phe Ser Ile Gly Thr Asn Ile His
1               5                   10

<210> SEQ ID NO 33
<211> LENGTH: 11
<212> TYPE: PRT
<213> ORGANISM: Artificial
<220> FEATURE:
<223> OTHER INFORMATION: Synthetic construct

<400> SEQUENCE: 33

Arg Ala Ser Tyr Ser Ile Gly Thr Asn Ile His
1               5                   10

<210> SEQ ID NO 34
<211> LENGTH: 11
<212> TYPE: PRT
<213> ORGANISM: Artificial
<220> FEATURE:
<223> OTHER INFORMATION: Synthetic construct

<400> SEQUENCE: 34

Arg Ala Ser His Ser Ile Gly Thr Asn Ile His
1               5                   10

<210> SEQ ID NO 35
<211> LENGTH: 7
<212> TYPE: PRT
<213> ORGANISM: Artificial
<220> FEATURE:
<223> OTHER INFORMATION: Synthetic construct

<400> SEQUENCE: 35

Tyr Ala Ser Glu Ser Ile Ser
1               5

<210> SEQ ID NO 36
<211> LENGTH: 9
<212> TYPE: PRT
<213> ORGANISM: Artificial
<220> FEATURE:
<223> OTHER INFORMATION: Synthetic construct
```

```
<400> SEQUENCE: 36

Gln Gln Asn Asn Asp Trp Pro Thr Thr
1               5

<210> SEQ ID NO 37
<211> LENGTH: 9
<212> TYPE: PRT
<213> ORGANISM: Artificial
<220> FEATURE:
<223> OTHER INFORMATION: Synthetic construct

<400> SEQUENCE: 37

Gln Gln Asn Asn Glu Trp Pro Thr Ser
1               5

<210> SEQ ID NO 38
<211> LENGTH: 9
<212> TYPE: PRT
<213> ORGANISM: Artificial
<220> FEATURE:
<223> OTHER INFORMATION: Synthetic construct

<400> SEQUENCE: 38

Gln Gln Asn Asn Asp Trp Pro Thr Ser
1               5

<210> SEQ ID NO 39
<211> LENGTH: 9
<212> TYPE: PRT
<213> ORGANISM: Artificial
<220> FEATURE:
<223> OTHER INFORMATION: Synthetic construct

<400> SEQUENCE: 39

Gln Gln Asn Asn Glu Trp Pro Thr Ser
1               5

<210> SEQ ID NO 40
<211> LENGTH: 9
<212> TYPE: PRT
<213> ORGANISM: Artificial
<220> FEATURE:
<223> OTHER INFORMATION: Synthetic construct

<400> SEQUENCE: 40

Gln Gln Asn Asn Lys Trp Pro Thr Ser
1               5

<210> SEQ ID NO 41
<211> LENGTH: 9
<212> TYPE: PRT
<213> ORGANISM: Artificial
<220> FEATURE:
<223> OTHER INFORMATION: Synthetic construct

<400> SEQUENCE: 41

Gln Gln Asn Asn Glu Trp Pro Thr Thr
1               5

<210> SEQ ID NO 42
<211> LENGTH: 9
<212> TYPE: PRT
<213> ORGANISM: Artificial
<220> FEATURE:
<223> OTHER INFORMATION: Synthetic construct

<400> SEQUENCE: 42
```

```
Gln Gln Asn Asn Asp Trp Pro Thr Thr
1               5

<210> SEQ ID NO 43
<211> LENGTH: 10
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: X is T or S
<220> FEATURE:
<221> NAME/KEY: MISC_FEATURE
<222> LOCATION: (7)..(7)
<223> OTHER INFORMATION: X is Y or W
<220> FEATURE:
<221> NAME/KEY: MISC_FEATURE
<222> LOCATION: (8)..(8)
<223> OTHER INFORMATION: X is G, E, D, or A

<400> SEQUENCE: 43

Gly Phe Ser Leu Xaa Asn Xaa Xaa Val His
1               5                   10

<210> SEQ ID NO 44
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is V or N
<220> FEATURE:
<221> NAME/KEY: MISC_FEATURE
<222> LOCATION: (7)..(7)
<223> OTHER INFORMATION: X is N, A, S or T
<220> FEATURE:
<221> NAME/KEY: MISC_FEATURE
<222> LOCATION: (8)..(8)
<223> OTHER INFORMATION: X is T or P
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X is T, D, A or N
<220> FEATURE:
<221> NAME/KEY: misc_feature
<222> LOCATION: (16)..(16)
<223> OTHER INFORMATION: Xaa can be any naturally occurring amino acid

<400> SEQUENCE: 44

Xaa Ile Trp Ser Ser Gly Gly Xaa Xaa Asp Tyr Asn Thr Pro Phe Xaa
1               5                   10                  15

Ser

<210> SEQ ID NO 45
<211> LENGTH: 11
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: X is T or D
```

```
<220> FEATURE:
<221> NAME/KEY: MISC_FEATURE
<222> LOCATION: (8)..(8)
<223> OTHER INFORMATION: X is E, N or D
<220> FEATURE:
<221> NAME/KEY: MISC_FEATURE
<222> LOCATION: (9)..(9)
<223> OTHER INFORMATION: X is F or Y

<400> SEQUENCE: 45

Ala Leu Xaa Tyr Tyr Asp Tyr Xaa Xaa Ala Tyr
1               5                   10

<210> SEQ ID NO 46
<211> LENGTH: 11
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: X is Q, E, F, Y or H

<400> SEQUENCE: 46

Arg Ala Ser Xaa Ser Ile Gly Thr Asn Ile His
1               5                   10

<210> SEQ ID NO 47
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: X is N, D, E or K
<220> FEATURE:
<221> NAME/KEY: MISC_FEATURE
<222> LOCATION: (9)..(9)
<223> OTHER INFORMATION: X is T or S

<400> SEQUENCE: 47

Gln Gln Asn Asn Xaa Trp Pro Thr Xaa
1               5

<210> SEQ ID NO 48
<211> LENGTH: 6
<212> TYPE: PRT
<213> ORGANISM: Artificial
<220> FEATURE:
<223> OTHER INFORMATION: Synthetic construct

<400> SEQUENCE: 48

Val Ile Cys Lys Ile Gly
1               5

<210> SEQ ID NO 49
<211> LENGTH: 119
<212> TYPE: PRT
<213> ORGANISM: Artificial
<220> FEATURE:
<223> OTHER INFORMATION: Synthetic construct

<400> SEQUENCE: 49

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Trp
```

-continued

```
                20                  25                  30

Gly Val His Trp Ile Arg Gln Pro Pro Gly Lys Ala Leu Glu Trp Leu
            35                  40                  45

Ala Val Ile Trp Ser Gly Gly Asn Thr Asp Tyr Asn Thr Pro Phe Asp
 50                  55                  60

Ser Arg Leu Thr Ile Ser Lys Asp Thr Ser Lys Ser Gln Val Val Leu
 65                  70                  75                  80

Thr Met Thr Asn Met Asp Pro Val Asp Thr Ala Thr Tyr Tyr Cys Ala
                 85                  90                  95

Arg Ala Leu Asp Tyr Tyr Asp Tyr Asp Phe Ala Tyr Trp Gly Gln Gly
             100                 105                 110

Thr Met Val Thr Val Ser Ser
            115

<210> SEQ ID NO 50
<211> LENGTH: 119
<212> TYPE: PRT
<213> ORGANISM: Artificial
<220> FEATURE:
<223> OTHER INFORMATION: Synthetic construct

<400> SEQUENCE: 50

Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Asn Trp
             20                  25                  30

Asp Val His Trp Ile Arg Gln Pro Pro Gly Lys Ala Leu Glu Trp Leu
             35                  40                  45

Ala Val Ile Trp Ser Gly Gly Asn Thr Asp Tyr Asn Thr Pro Phe Ala
 50                  55                  60

Ser Arg Leu Thr Ile Ser Lys Asp Thr Ser Lys Ser Gln Val Val Leu
 65                  70                  75                  80

Thr Met Thr Asn Met Asp Pro Val Asp Thr Ala Thr Tyr Tyr Cys Ala
                 85                  90                  95

Arg Ala Leu Asp Tyr Tyr Asp Tyr Asn Phe Ala Tyr Trp Gly Gln Gly
             100                 105                 110

Thr Met Val Thr Val Ser Ser
            115

<210> SEQ ID NO 51
<211> LENGTH: 119
<212> TYPE: PRT
<213> ORGANISM: Artificial
<220> FEATURE:
<223> OTHER INFORMATION: Synthetic construct

<400> SEQUENCE: 51

Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Asn Trp
             20                  25                  30

Asp Val His Trp Ile Arg Gln Pro Pro Gly Lys Ala Leu Glu Trp Leu
             35                  40                  45

Ala Val Ile Trp Ser Gly Gly Ala Thr Asp Tyr Asn Thr Pro Phe Asn
 50                  55                  60

Ser Arg Leu Thr Ile Ser Lys Asp Thr Ser Lys Ser Gln Val Val Leu
 65                  70                  75                  80
```

```
Thr Met Thr Asn Met Asp Pro Val Asp Thr Ala Thr Tyr Tyr Cys Ala
                85                  90                  95

Arg Ala Leu Asp Tyr Tyr Asp Tyr Asn Phe Ala Tyr Trp Gly Gln Gly
            100                 105                 110

Thr Met Val Thr Val Ser Ser
        115

<210> SEQ ID NO 52
<211> LENGTH: 119
<212> TYPE: PRT
<213> ORGANISM: Artificial
<220> FEATURE:
<223> OTHER INFORMATION: Synthetic construct

<400> SEQUENCE: 52

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Trp
            20                  25                  30

Asp Val His Trp Ile Arg Gln Pro Pro Gly Lys Ala Leu Glu Trp Leu
        35                  40                  45

Ala Val Ile Trp Ser Gly Gly Asn Thr Asp Tyr Asn Thr Pro Phe Thr
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Asp Tyr Tyr Asp Tyr Glu Phe Ala Tyr Trp Gly Gln Gly
            100                 105                 110

Thr Met Val Thr Val Ser Ser
        115

<210> SEQ ID NO 53
<211> LENGTH: 119
<212> TYPE: PRT
<213> ORGANISM: Artificial
<220> FEATURE:
<223> OTHER INFORMATION: Synthetic construct

<400> SEQUENCE: 53

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Trp
            20                  25                  30

Asp Val His Trp Ile Arg Gln Pro Pro Gly Lys Ala Leu Glu Trp Leu
        35                  40                  45

Ala Val Ile Trp Ser Gly Gly Asn Thr Asp Tyr Asn Thr Pro Phe Thr
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Asp Tyr Tyr Asp Tyr Asp Phe Ala Tyr Trp Gly Gln Gly
            100                 105                 110

Thr Met Val Thr Val Ser Ser
        115

<210> SEQ ID NO 54
```

```
<211> LENGTH: 119
<212> TYPE: PRT
<213> ORGANISM: Artificial
<220> FEATURE:
<223> OTHER INFORMATION: Synthetic construct

<400> SEQUENCE: 54

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Trp
            20                  25                  30

Asp Val His Trp Ile Arg Gln Pro Pro Gly Lys Gly Leu Glu Trp Ile
        35                  40                  45

Gly Asn Ile Trp Ser Gly Gly Asn Thr Asp Tyr Asn Thr Pro Phe Thr
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Leu Asp Tyr Tyr Asp Tyr Asp Tyr Ala Tyr Trp Gly Gln Gly
            100                 105                 110

Thr Met Val Thr Val Ser Ser
        115

<210> SEQ ID NO 55
<211> LENGTH: 119
<212> TYPE: PRT
<213> ORGANISM: Artificial
<220> FEATURE:
<223> OTHER INFORMATION: Synthetic construct

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Ile Arg Gln Pro Pro Gly Lys Gly Leu Glu Trp Ile
        35                  40                  45

Gly Asn Ile Trp Ser Gly Gly Asn Thr Asp Tyr Asn Thr Pro Phe Thr
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Leu Asp Tyr Tyr Asp Tyr Asp Tyr Ala Tyr Trp Gly Gln Gly
            100                 105                 110

Thr Met Val Thr Val Ser Ser
        115

<210> SEQ ID NO 56
<211> LENGTH: 119
<212> TYPE: PRT
<213> ORGANISM: Artificial
<220> FEATURE:
<223> OTHER INFORMATION: Synthetic construct

<400> SEQUENCE: 56

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Thr Asn Trp
            20                  25                  30

Asp Val His Trp Ile Arg Gln Pro Gly Lys Gly Leu Glu Trp Ile
        35                  40                  45

Gly Val Ile Trp Ser Gly Gly Asn Thr Asp Tyr Asn Thr Pro Phe Thr
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Leu Asp Tyr Tyr Asp Tyr Asp Phe Ala Tyr Trp Gly Gln Gly
            100                 105                 110

Thr Met Val Thr Val Ser Ser
        115
```

<210> SEQ ID NO 57
<211> LENGTH: 25
<212> TYPE: PRT
<213> ORGANISM: Homo sapiens

<400> SEQUENCE: 57

```
Gln Val Thr Leu Lys Glu Ser Gly Pro Val Leu Val Lys Pro Thr Glu
 1               5                  10                  15

Thr Leu Thr Leu Thr Cys Thr Val Ser
            20                  25
```

<210> SEQ ID NO 58
<211> LENGTH: 14
<212> TYPE: PRT
<213> ORGANISM: Homo sapiens

<400> SEQUENCE: 58

```
Trp Ile Arg Gln Pro Pro Gly Lys Ala Leu Glu Trp Leu Ala
 1               5                  10
```

<210> SEQ ID NO 59
<211> LENGTH: 32
<212> TYPE: PRT
<213> ORGANISM: Homo sapiens

<400> SEQUENCE: 59

```
Arg Leu Thr Ile Ser Lys Asp Thr Ser Lys Ser Gln Val Val Leu Thr
 1               5                  10                  15

Met Thr Asn Met Asp Pro Val Asp Thr Ala Thr Tyr Tyr Cys Ala Arg
            20                  25                  30
```

<210> SEQ ID NO 60
<211> LENGTH: 10
<212> TYPE: PRT
<213> ORGANISM: Homo sapiens

<400> SEQUENCE: 60

```
Gly Gln Gly Thr Met Val Thr Val Ser Ser
 1               5                  10
```

<210> SEQ ID NO 61
<211> LENGTH: 25
<212> TYPE: PRT
<213> ORGANISM: Homo sapiens

<400> SEQUENCE: 61

```
Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 62
<211> LENGTH: 14
<212> TYPE: PRT
<213> ORGANISM: Homo sapiens

<400> SEQUENCE: 62

Trp Ile Arg Gln Pro Pro Gly Lys Gly Leu Glu Trp Ile Gly
1               5                   10

<210> SEQ ID NO 63
<211> LENGTH: 32
<212> TYPE: PRT
<213> ORGANISM: Homo sapiens

<400> SEQUENCE: 63

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 64
<211> LENGTH: 10
<212> TYPE: PRT
<213> ORGANISM: Homo sapiens

<400> SEQUENCE: 64

Gly Gln Gly Thr Met Val Thr Val Ser Ser
1               5                   10

<210> SEQ ID NO 65
<211> LENGTH: 7
<212> TYPE: PRT
<213> ORGANISM: Artificial
<220> FEATURE:
<223> OTHER INFORMATION: Synthetic construct

<400> SEQUENCE: 65

Met Ala Arg Tyr Ala Asn Asn
1               5

<210> SEQ ID NO 66
<211> LENGTH: 107
<212> TYPE: PRT
<213> ORGANISM: Artificial
<220> FEATURE:
<223> OTHER INFORMATION: Synthetic construct

<400> SEQUENCE: 66

Glu Ile Val Leu Thr Gln Ser Pro Asp Phe Gln Ser Val Thr Pro Lys
1               5                   10                  15

Glu Lys Val Thr Ile Thr Cys Arg Ala Ser Tyr Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80
```

```
Glu Asp Ala Ala Thr Tyr Tyr Cys Gln Gln Asn Asn Glu Trp Pro Thr
                85                  90                  95

Ser Phe Gly Gly Gly Thr Lys Val Glu Ile Lys
            100                 105

<210> SEQ ID NO 67
<211> LENGTH: 107
<212> TYPE: PRT
<213> ORGANISM: Artificial
<220> FEATURE:
<223> OTHER INFORMATION: Synthetic construct

<400> SEQUENCE: 67

Glu Ile Val Leu Thr Gln Ser Pro Asp Phe Gln Ser Val Thr Pro Lys
1               5                   10                  15

Glu Lys Val Thr Ile Thr Cys Arg Ala Ser Tyr Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Ser Phe Gly Gly Gly Thr Lys Val Glu Ile Lys
            100                 105

<210> SEQ ID NO 68
<211> LENGTH: 107
<212> TYPE: PRT
<213> ORGANISM: Artificial
<220> FEATURE:
<223> OTHER INFORMATION: Synthetic construct

<400> SEQUENCE: 68

Glu Ile Val Leu Thr Gln Ser Pro Asp Phe Gln Ser Val Thr Pro Lys
1               5                   10                  15

Glu Lys Val Thr Ile Thr Cys Arg Ala Ser Tyr Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Gly Gly Thr Lys Val Glu Ile Lys
            100                 105

<210> SEQ ID NO 69
<211> LENGTH: 107
<212> TYPE: PRT
<213> ORGANISM: Artificial
<220> FEATURE:
<223> OTHER INFORMATION: Synthetic construct

<400> SEQUENCE: 69
```

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Tyr Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Glu Trp Pro Thr
                85                  90                  95

Ser Phe Gly Gly Gly Thr Lys Val Glu Ile Lys
            100                 105
```

<210> SEQ ID NO 70
<211> LENGTH: 107
<212> TYPE: PRT
<213> ORGANISM: Artificial
<220> FEATURE:
<223> OTHER INFORMATION: Synthetic construct

<400> SEQUENCE: 70

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Tyr Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asp Trp Pro Thr
                85                  90                  95

Thr Phe Gly Gly Gly Thr Lys Val Glu Ile Lys
            100                 105
```

<210> SEQ ID NO 71
<211> LENGTH: 107
<212> TYPE: PRT
<213> ORGANISM: Artificial
<220> FEATURE:
<223> OTHER INFORMATION: Synthetic construct

<400> SEQUENCE: 71

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Tyr Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asp Trp Pro Thr
                85                  90                  95
```

Thr Phe Gly Gly Gly Thr Lys Val Glu Ile Lys
            100                 105

<210> SEQ ID NO 72
<211> LENGTH: 107
<212> TYPE: PRT
<213> ORGANISM: Artificial
<220> FEATURE:
<223> OTHER INFORMATION: Synthetic construct

<400> SEQUENCE: 72

Glu Ile Val Leu Thr Gln Ser Pro Asp Phe Gln Ser Val Thr Pro Lys
1               5                   10                  15

Glu Lys Val Thr Ile Thr Cys Arg Ala Ser Tyr Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Glu Trp Pro Thr
                85                  90                  95

Ser Phe Gly Gly Gly Thr Lys Val Glu Ile Lys
            100                 105

<210> SEQ ID NO 73
<211> LENGTH: 107
<212> TYPE: PRT
<213> ORGANISM: Artificial
<220> FEATURE:
<223> OTHER INFORMATION: Synthetic construct

<400> SEQUENCE: 73

Glu Ile Val Leu Thr Gln Ser Pro Asp Phe Gln Ser Val Thr Pro Lys
1               5                   10                  15

Glu Lys Val Thr Ile Thr Cys Arg Ala Ser Tyr Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asp Trp Pro Thr
                85                  90                  95

Ser Phe Gly Gly Gly Thr Lys Val Glu Ile Lys
            100                 105

<210> SEQ ID NO 74
<211> LENGTH: 23
<212> TYPE: PRT
<213> ORGANISM: Homo sapiens

<400> SEQUENCE: 74

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 75
<211> LENGTH: 15
<212> TYPE: PRT
<213> ORGANISM: Homo sapiens

<400> SEQUENCE: 75

Trp Tyr Gln Gln Lys Pro Asp Gln Ser Pro Lys Leu Leu Ile Lys
1               5                   10                  15

<210> SEQ ID NO 76
<211> LENGTH: 32
<212> TYPE: PRT
<213> ORGANISM: Homo sapiens

<400> SEQUENCE: 76

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 77
<211> LENGTH: 10
<212> TYPE: PRT
<213> ORGANISM: Homo sapiens

<400> SEQUENCE: 77

Phe Gly Gly Gly Thr Lys Val Glu Ile Lys
1               5                   10

<210> SEQ ID NO 78
<211> LENGTH: 45
<212> TYPE: DNA
<213> ORGANISM: Homo sapiens

<400> SEQUENCE: 78
taaggtaccg ctcttcgggg agccaccatg ggaccctccg ggacg                45

<210> SEQ ID NO 79
<211> LENGTH: 36
<212> TYPE: DNA
<213> ORGANISM: Homo sapiens

<400> SEQUENCE: 79
gctcttcggg gagcagccat gcgaccctcc gggacg                          36

<210> SEQ ID NO 80
<211> LENGTH: 5
<212> TYPE: PRT
<213> ORGANISM: Artificial
<220> FEATURE:
<223> OTHER INFORMATION: Synthetic construct

<400> SEQUENCE: 80

Gly Gly Gly Gly Ser
1               5

<210> SEQ ID NO 81
<211> LENGTH: 6
<212> TYPE: PRT
<213> ORGANISM: Artificial
<220> FEATURE:
<223> OTHER INFORMATION: Synthetic construct

<400> SEQUENCE: 81

```
His His His His His His
1               5

<210> SEQ ID NO 82
<211> LENGTH: 72
<212> TYPE: DNA
<213> ORGANISM: Homo sapiens

<400> SEQUENCE: 82
atgtctagaa actcaatggt gatggtgatg atgcgagcca ccgccaccga tcttaggccc    60
attcgttgga ca                                                        72
```

ANTI-EGFR ANTIBODIES

This U.S. national phase application of PCT/US2006/043311, filed Nov. 6, 2006, claims priority to U.S. provisional patent application Ser. No. 60/735,363, filed Nov. 12, 2005.

FIELD OF THE INVENTION

The invention is in the field of medicine, particularly in the field of monoclonal antibodies against epidermal growth factor receptor (EGFR). More specifically the invention relates to high affinity, humanized anti-EGFR antibodies and use of the antibodies for therapy, prophylaxis or diagnosis of various cancers.

BACKGROUND OF THE INVENTION

The epidermal growth factor receptor (EGFR) is a member of the tyrosine kinase family of cell surface receptors that are widely expressed in epithelial, mesenchymal and neuronal tissues and play fundamental roles during development and differentiation. EGFR, also known as HER1 or c-erbB-1, is a 170 kDa transmembrane glycoprotein consisting of an extracellular ligand binding domain, a transmembrane region and an intracellular domain with tyrosine kinase activity (Ullrich et al., Human Epidermal Growth Factor cDNA Sequence and Aberrant Expression of the Amplified Gene in A-431 Epidermoid Carcinoma Cells, Nature, Vol. 309, 418-25 (1986)). Mammalian ligands that bind and activate EGFR include EGF, transforming growth factor α (TGFα), heparin-binding EGF-like growth factor, amphiregulin, betacellulin, epiregulin, and epigen (Singh, A. and Harris, R., 2005, *Cellular Signaling* 17:1183-1193). The binding of growth factors EGF or transforming growth factor α (TGFα) to the epidermal growth factor receptor results in receptor dimerization, autophosphorylation and induction of a tyrosine kinase cascade, leading ultimately to DNA synthesis and cell division.

EGFR is abnormally activated in many epithelial tumors, including those in non-small cell lung cancer, breast cancer, colorectal cancer, head and neck cancers, and prostate cancer (Adams, G. and Weiner, L., 2005, Nature Biotechnology, 23:1147-1157). Abnormal activation of EGFR can arise from overexpression of the receptor, gene amplification, activating mutations, overexpression of receptor ligands, and/or loss of regulators of EGFR activity (Baselga, J. and Arteaga, C., 2005, J. of Clin. Oncol. 23:2445-2459). Abnormally high EGFR activation results in phosphorylation of several intracellular substrates, which in turns gives rise to mitogenic signaling as well as other tumor-inducing activities. Consequently, EGFR is a target for anti-cancer therapeutic strategies which can potentially inhibit or reduce the receptor's aberrant expression.

Anti-cancer agents that target EGFR include monoclonal antibodies. The chimeric monoclonal antibody C225 (or cetuximab), which contains the murine variable region of mAb225 and a human IgG1 constant region, is presently available for treatment of irinotecan-refractory colon cancer in the United States and Europe (Baselga, J. and Arteaga, C., 2005, J. of Clin. Oncol. 23:2445-2459). In addition both human and humanized monoclonal antibodies to EGFR have been studied. The fully human antibody ABX-EGF (panitumumab) has an affinity for EGFR approximately 8-fold greater than that of C225 (Yang, X-D et al., 2001, Crit. Rev. Oncol./Hemat., 38:17-23). The affinity of humanized antibody EMD72000 (matuzumab) for EGFR is similar to that of C225 (Vanhoefer, U. et al., 2004, J. Clin Oncol., 22:175-184), and the affinity of humanized antibody h-R3 for EGFR is less than that of C225 (Crombet, T. et al., 2004, J. Clin. Oncol., 22:1646-1654). Complications have been observed in the clinic with doses of cetuximab higher than 100 mg/m². They include skin toxicity that results in flushing, seborrheic dermatitis, and acneform rash (Herbst, R. and Langer, C., 2002, Semin. Oncol. 29:27-36).

There is a therapeutic need for an anti-EGFR antibody that binds EGFR with a high affinity and inhibits the abnormal activation of EGFR in epithelial tumors. A high affinity anti-EGFR antibody would allow lower doses to be administered to eliminate potential side effects such as skin toxicity. Moreover, there is a need to provide an anti-EGFR antibody that mitigates any potential immune response to the antibody that could be induced through multiple dosing. The present invention satisfies these needs and provides related advantages.

SUMMARY OF THE INVENTION

Antibodies of the invention are humanized EGFR specific monoclonal antibodies, and antigen-binding portions thereof, that inhibit activation of EGFR. In one embodiment, the antibodies of the invention are characterized by high affinity binding to EGFR, wherein an anti-EGFR monoclonal antibody has an EGFR binding affinity (Kd) of between about 0.01 pM and about 10 pM. In a preferred embodiment, the antibodies of the invention have a Kd (with EGFR) no greater than 10 pM, preferably a Kd no greater than 9, 8, 7, 6, 5, 4, 3, 2 or 1 pM, and even more preferably a Kd no greater than 0.8, 0.6, 0.4, 0.2, 0.08, 0.06, 0.04, 0.02 or 0.01 pM.

In one embodiment, an EGFR specific monoclonal antibody comprises a HCDR1 comprising the amino acid sequence as shown in SEQ ID NO: 43, a HCDR2 comprising the amino acid sequence as shown in SEQ ID NO: 44, a HCDR3 comprising the amino acid sequence as shown in SEQ ID NO: 45, a LCDR1 comprising the amino acid sequence as shown in SEQ ID NO: 46, a LCDR2 comprising the amino acid sequence as shown in SEQ ID NO: 35 and a LCDR3 comprising the amino acid sequence as shown in SEQ ID NO: 47. Preferably this antibody is further characterized as inhibiting activation of EGFR. Preferably this antibody is further characterized as having a binding affinity with EGFR (Kd) no greater than 10 pM, preferably a Kd no greater than 9, 8, 7, 6, 5, 4, 3, 2 or 1 pM, and even more preferably a Kd no greater than 0.8, 0.6, 0.4, 0.2, 0.08, 0.06, 0.04, 0.02 or 0.01 pM. More preferably this antibody is further characterized as inhibiting activation of EGFR and having a binding affinity with EGFR no greater than 10 pM, preferably a Kd no greater than 9, 8, 7, 6, 5, 4, 3, 2 or 1 pM, and even more preferably a Kd no greater than 0.8, 0.6, 0.4, 0.2, 0.08, 0.06, 0.04, 0.02 or 0.01 pM.

In one embodiment of the invention, an EGFR specific monoclonal antibody of the invention comprises a heavy chain variable region (HCVR) of SEQ ID NO:49 and a light chain variable region (LCVR) of SEQ ID NO:66. In other embodiments, an EGFR specific monoclonal antibody comprises a HCVR of SEQ ID NO:51 and a LCVR of SEQ ID NO:68; a HCVR of SEQ ID NO:55 and a LCVR of SEQ ID NO:72; or a HCVR of SEQ ID NO:56 and a LCVR of SEQ ID NO:73.

Another embodiment of the present invention includes the monoclonal antibody of any of the above embodiments wherein the antibody is a full-length antibody, a substantially intact antibody, a Fab fragment, a F(ab')₂ fragment, or a single chain Fv fragment. Preferably, the antibody, or antigen-binding portion thereof, of any of the above embodiments is a humanized antibody.

The invention includes isolated nucleic acid molecules comprising polynucleotides that encode the antibodies described herein and vectors, preferably expression vectors, comprising said nucleic acid molecules. The invention also encompasses host cells transfected with vectors containing these polynucleotides that express the antibodies described herein.

The invention encompasses a method of treating an EGFR mediated cancer which comprises administering to a subject an effective amount of an antibody described herein.

Finally, the invention encompasses the use of an antibody described herein for the manufacture of a medicament for treating an EGFR mediated cancer in a subject in need thereof.

DETAILED DESCRIPTION OF THE INVENTION

Definitions

Figure 1:
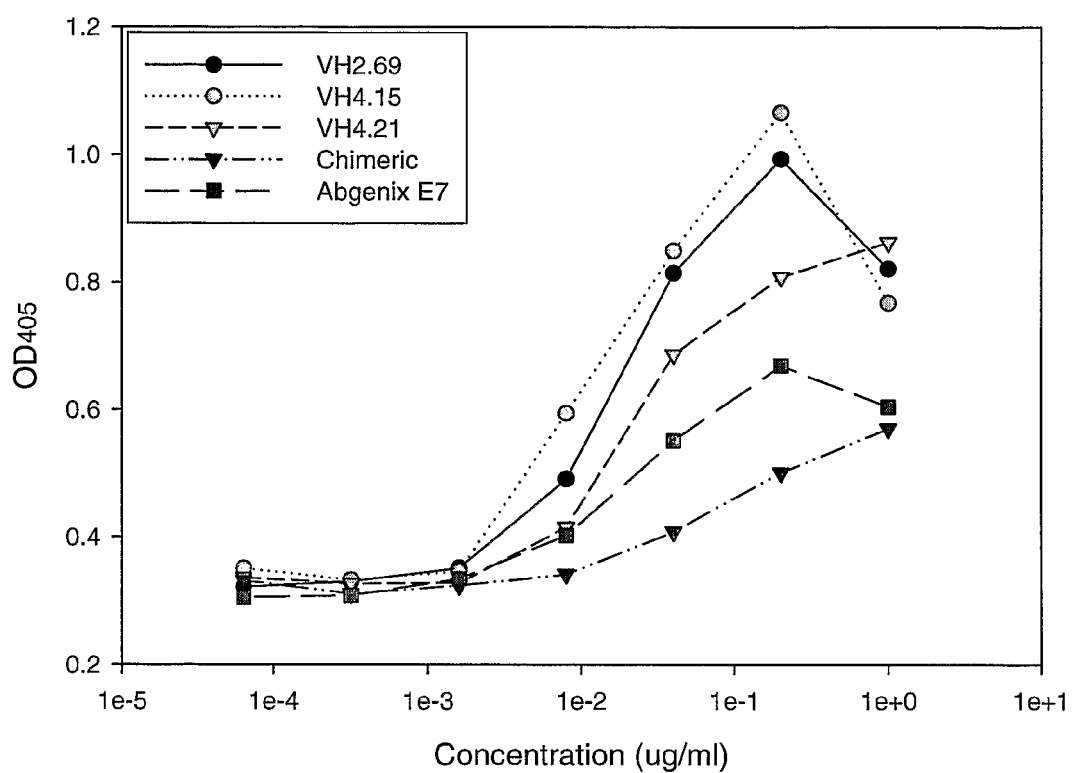
FIG. 1. shows the results of a capture ELISA with Fabs 2.69, 4.15, 4.21, chimeric antibody C225, and human antibody AGX-EGF.

As used herein, "epidermal growth factor receptor" or "EGFR" refers to the mature, tyrosine kinase cell surface receptor. The term "soluble EGFR" or "sEGFR" refers to a portion of EGFR containing the extracellular, ligand-binding domain of EGFR. More specifically, sEGFR contains amino acids 1-619 of mature EGFR (Ullrich et al., Human Epidermal Growth Factor cDNA Sequence and Aberrant Expression of the Amplified Gene in A-431 Epidermoid Carcinoma Cells, Nature, Vol. 309, 418-25 (1986)).

The phrase "EGFR mediated cancer" refers to a cancer characterized by epithelial tumors in which EGFR is abnormally activated to levels greater than in normal, corresponding epithelial tissue. These greater levels of EGFR activity promote tumor growth in many types of cancer. Such cancers include, but are not limited to, non-small cell lung cancer, breast cancer, colorectal cancer, head and neck cancers, and prostate cancer. Abnormal activation of EGFR can arise from overexpression of the receptor, gene amplification, activating mutations, overexpression of receptor ligands, and/or loss of regulators of EGFR activity.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Assignment of amino acids to each domain generally is in accordance with well-known conventions (e.g., Kabat, "Sequences of Proteins of Immunological Interest," National Institutes of Health, Bethesda, Md. (1991) or Chothia numbering scheme as described in Al-Lazikani et al., *J. Mol. Biol.* 273:927-948, 1997). The CDRs of the VH are referred to herein as HCDR1, HCDR2 and HCDR3. The CDRs of the VL are referred to herein as LCDR1, LCDR2 and LCDR3.

Light chains are classified as kappa and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 3 or more amino acids.

In accordance with the foregoing, the antibodies of the present invention are monoclonal antibodies. Such antibodies, however, are monoclonal only in the sense that they may be derived from a clone of a single cell type. However, this is not meant to limit them to a particular origin. Such antibodies may readily be produced in cells that commonly do not produce antibodies, such as CHO, NS0, or COS cells. In addition, such antibodies may be produced in other types of cells, especially mammalian and even plant cells, by genetically engineering such cells to express and assemble the polypeptide light and heavy chains forming the antibody product. In addition, such chains can be chemically synthesized but, since they would be specific for a given antigenic determinant, would still constitute "monoclonal" antibodies within the spirit in which that term is used. Thus, as used herein, the term monoclonal antibody is intended to denote more the specificity and purity of the antibody molecules rather than the mere mechanism used for production of said antibodies.

The term "antigen-binding portion" of an antibody, as used herein, refers to that portion of an antibody molecule, within the variable region, that is required to bind the antigen of interest. The antigen-binding portion contains the amino acid residues that interact with an antigen and confer on the antibody its specificity and affinity for the antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, and (v) a dAb fragment (Ward et al., (1989) Nature 341: 544-546), which consists of a VH domain. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426: and Huston et al. (1988) Proc. Natl. Acad. Sci. USA 85: 5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

The term "humanized antibody" means an antibody that is composed partially or fully of amino acid sequences derived from a human antibody germline or a rearranged sequence and made by combining such sequences with non-human complementarity determining regions (CDRs). The framework regions of the variable regions are substituted by fully human or substantially human framework regions. In a humanized antibody for therapeutic use in humans, the framework sequence is preferably entirely or substantially of human origin (i.e., at least 90%, 92%, 95%, 96%, 97%, 98% or 99% of human origin). The CDRs of a humanized antibody may be optimized from the CDRs of a non-human antibody from which they originated to generate desired properties, e.g., specificity, affinity and capacity. Optimized CDRs may have amino acid substitutions, additions and/or deletions when compared to the original, non-human CDRs. As discussed herein, antibody in the context of humanized antibody is not limited to a full-length antibody and can include antigen portions thereof, such as fragments and single chain forms.

The term "human antibody", as used herein, is intended to include human antibodies as well as those that are prepared, expressed, created or isolated by recombinant means. Human antibodies generated by recombinant means include antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucleic Acids Res. 20: 6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis and thus the amino acid sequences of the VH and VL regions of the recombinant antibodies are sequences that, while derived from and related to human germline VH and VL sequences, may not naturally exist within the human antibody germline repertoire in vivo.

The phrases "biological property" or "biological activity," in reference to an antibody of the present invention, are used interchangeably herein and include, but are not limited to, epitope/antigen affinity and specificity, ability to neutralize or antagonize an activity of EGFR in vivo or in vitro, and the in vivo stability of the antibody and the immunogenic properties of the antibody. Other identifiable biological properties of an antibody include, for example, specificity, cross-reactivity, (i.e., with non-human homologs of the targeted peptide, or with other proteins or tissues, generally), and ability to preserve high expression levels of protein in mammalian cells. The aforementioned properties or characteristics can be observed or measured or assessed using art-recognized techniques including, but not limited to, ELISA, competitive ELISA, surface plasmon resonance analysis, in vitro and in vivo neutralization assays, receptor binding, and immunohistochemistry with tissue sections from different sources including human or any other source as the need may be.

The term "inhibit" as used herein with respect to an activity of an antibody of the invention means the ability to substantially antagonize, prohibit, prevent, restrain, slow, disrupt, eliminate, stop, reduce or reverse e.g., progression or severity of that which is being inhibited including, but not limited to, a biological activity or property, a disease or a condition. The inhibition or neutralization is preferably at least about 10%, 20%, 30%, 40%, 50%, 60%, 70%, 80%, 90%, 95% or higher.

The phrase "ability to inhibit EGFR activation" with respect to an antibody as used herein, is intended to refer to an antibody whose binding to EGFR results in inhibition of human EGFR activation and the biological activity of human EGFR that occurs upon activation of the receptor. Measuring one or more indicators of EGFR biological activity as determined using either a cell proliferation assay, an apoptosis assay, a receptor binding assay, a receptor phosphorylation assay, or a mouse tumor model (see Examples 6-10) can assess an antibody's ability to inhibit EGFR activation.

An "isolated antibody", as used herein, is intended to refer to an antibody that is substantially free of other antibodies having different antigenic specificities (e.g., an isolated antibody that binds EGFR is substantially free of antibodies that specifically bind other antigens). An isolated antibody that specifically binds the human EGFR may, however, have cross-reactivity to other antigens, such as EGFR molecules from other species. Moreover, an isolated antibody may be substantially free of other cellular material and/or chemicals.

The term "$k_{on}$", as used herein is intended to refer to the association or on rate constant, or specific reaction rate, of the forward, or complex-forming, reaction, measured in units: $M^{-1}sec^{-1}$.

The term "$k_{off}$", as used herein, is intended to refer to the dissociation or off rate constant, or specific reaction rate, for dissociation of an antibody from the antibody/antigen complex, measured in units: $sec^{-1}$.

The term "Kd", as used herein, is intended to refer to the dissociation constant of a particular antibody-antigen interaction. It is calculated by the formula:

$$k_{off}/k_{on}=K_d$$

The antibodies of the present invention are high affinity antibodies, generally exhibiting low $k_{off}$ values. For purposes of the present disclosure, the term "high affinity" refers to an affinity or Kd of between $1\times10^{-11}$ M to about $1\times10^{-14}$M or further refers to an affinity or Kd no greater than 10, 9, 8, 7, 6, 5, 4, 3, 2, 1, 0.8, 0.6, 0.4, 0.2, 0.08, 0.06, 0.04, 0.02 or 0.01 pM.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind human EGFR is intended to refer to a nucleic acid molecule in which the nucleotide sequences encoding the antibody or antibody portion are free of other nucleotide sequences encoding antibodies or antibody portions that bind antigens other than human EGFR, which other sequences may naturally flank the nucleic acid in human genomic DNA. Thus, for example, an isolated nucleic acid of the invention encoding a VH region of an anti-human EGFR antibody contains no other sequences encoding other VH regions that bind antigens other than human EGFR.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome.

The term "recombinant host cell" (or simply "host cell"), as used herein, is intended to refer to a cell into which a recombinant expression vector has been introduced.

Antibody Characterization

A primary advantage of a humanized antibody is that immune responses due to repeated administration in patients are minimized. The more human sequences that are employed in a humanized antibody, the lower the risk of immunogenicity. In addition, the injected humanized antibodies generally have a longer half-life in the circulation than injected antibodies that are non-human or partially non-human.

As discussed herein, human framework variable regions and variants thereof may be used in the present invention. However, regardless of the framework chosen, if reducing the risk of immunogenicity is a focus, the number of changes relative to the human framework chosen are minimized.

The heavy and light chain variable region framework residues can be derived from the same or different human antibody sequences. The human antibody sequences can be the sequences of naturally occurring human antibodies or can be consensus sequences of several human antibodies. The humanized antibody of the present invention may comprise or be derived from a human germline light chain framework. Likewise, the humanized antibody of the present invention may comprise or be derived from a human germline heavy chain framework. The framework context of CDRs influences their binding to antigen, such that variation between difference frameworks may lead to some or significant loss of binding affinity to the antigen. In preferred embodiments of the present invention, the light chain framework is derived from human germline VK sequence A26. In preferred embodiments, the heavy chain human germline framework is selected from VH2-26 and VH4-59. See WO 2005/005604 for a description of different germline sequences.

Preferred human heavy chain constant region amino acid sequences of the humanized antibodies of the present invention include the IgG1 constant region or the IgG4 constant region, which are both well known in the art.

The present invention encompasses antibodies or antigen-binding portions thereof that bind to EGFR and inhibit the receptor's binding of ligands and subsequent activation. Thus, the CDRs and heavy and light chain variable regions described herein are used to make full-length antibodies as well as functional fragments that maintain the binding affinity of the protein employing the CDRs for EGFR binding.

The binding affinity of antibodies was determined using a Sapidyne KINEXA assay (see Example 7). Chimeric antibody C225 has a Kd of approximately 380 pM (picomolar). The humanized antibodies of the present invention, have a Kd of between about 0.01 and about 10 pM; about 0.1 and about 10 pM; about 0.1 and about 1 pM; about 0.2 and about 10 pM; about 0.2 and about 1 pM; about 0.6 and about 10 pM; and about 0.6 and about 1 pM. Preferably the humanized antibodies of the present invention have a Kd no greater than 10, 9, 8, 7, 6, 5, 4, 3, 2, 1, 0.8, 0.6, 0.4, 0.2, 0.08, 0.06, 0.04, 0.02 or 0.01 pM.

It is also preferred that the antibodies or antigen-binding portions thereof of the present invention inhibit the activation of EGFR Several assays are utilized to test the ability of antibodies of the present invention to inhibit EGFR activation (see Examples 6-10).

Sequence

Tables 1 and 2 indicate the amino acid sequences (using standard amino acid one letter code) of the CDRs employed in the antibodies of the present invention, which comprise one or more heavy and light chain CDRs. The CDRs are presented in the table in the context of individual antibody clones (Fab fragments). In Tables 1 and 2, the locations of amino acid substitutions made relative to the corresponding C225 CDRs (i.e., locations at which CDRs differ in amino acids) are indicated in bold and underlined. Tables 1 and 2 provide heavy and light chain CDRs. These CDRs were combined with human germline framework sequences as follows: Light chain CDRs were combined with framework sequence from VL A26. CDRs for Hu 2-26 through 2.II.10 in Table 1 have a heavy chain framework sequence from VH 2-26, while CDRs Hu 4-49 through 4.23 in Table 1 have a heavy chain framework sequence from VH 4-59. Exemplary HCVRs and LCVRs showing the CDRs in the context of the frameworks are shown below in Table 3.

TABLE 1

| CDR Sequences - Heavy Chain Variable Region (HCVR) | | | | | |
|---|---|---|---|---|---|
| Fab | HCDR1 | SEQ ID NO. | HCDR2 | SEQ ID NO. | HCDR3 | SEQ ID NO. |
| Hu 2-26 | GFSLTNYGVH | 1 | VIWSGGNTDYNTPFTS | 11 | ALDYYDYEFAY | 25 |
| 2-26.1 | GFSLTNWGVH | 2 | VIWSGGNTDYNTPFTS | 11 | ALDYYDYEFAY | 25 |
| 2-26.2 | GFSLTNYDVH | 3 | VIWSGGNTDYNTPFTS | 11 | ALDYYDYEFAY | 25 |
| 2-26.3 | GFSLTNYEVH | 4 | VIWSGGNTDYNTPFTS | 11 | ALDYYDYEFAY | 25 |
| 2-26.4 | GFSLTNYAVH | 5 | VIWSGGNTDYNTPFTS | 11 | ALDYYDYEFAY | 25 |
| 2-26.5 | GFSLTNYGVH | 1 | VIWSGGATDYNTPFTS | 12 | ALDYYDYEFAY | 25 |
| 2-26.6 | GFSLTNYGVH | 1 | VIWSGGSTDYNTPFTS | 13 | ALDYYDYEFAY | 25 |

TABLE 1-continued

CDR Sequences - Heavy Chain Variable Region (HCVR)

| Fab | HCDR1 | SEQ ID NO. | HCDR2 | SEQ ID NO. | HCDR3 | SEQ ID NO. |
|---|---|---|---|---|---|---|
| 2-26.7 | GFSLTNYGVH | 1 | VIWSGGNDDYNTPFDS | 14 | ALDYYDYEFAY | 25 |
| 2-26.8 | GFSLTNYGVH | 1 | VIWSGGNDDYNTPFNS | 11 | ALDYYDYEFAY | 25 |
| 2-26.9 | GFSLTNYGVH | 1 | VIWSGGNTDYNTPFTS | 11 | ALDYYDYNFAY | 26 |
| 2-26.10 | GFSLTNYGVH | 1 | VIWSGGNTDYNTPFTS | 11 | ALDYYDYDFAY | 27 |
| 2-26.11 | GFSLTNYGVH | 1 | VIWSGGNTDYNTPFTS | 11 | ALDYYDYEFAY | 25 |
| 2-26.12 | GFSLTNYGVH | 1 | VIWSGGNTDYNTPFTS | 11 | ALDYYDYEFAY | 25 |
| 2-26.13 | GFSLTNYGVH | 1 | VIWSGGNTDYNTPFTS | 11 | ALDYYDYEFAY | 25 |
| 2-26.14 | GFSLTNYGVH | 1 | VIWSGGNTDYNTPFTS | 11 | ALDYYDYEFAY | 25 |
| 2-26.15 | GFSLTNYGVH | 1 | VIWSGGNTDYNTPFTS | 11 | ALDYYDYEFAY | 25 |
| 2.21 | GFSLSNWGVH | 6 | VIWSGGATDYNTPFDS | 15 | ALDYYDYNFAY | 26 |
| 2.33 | GFSLSNWEVH | 7 | VIWSGGATDYNTPFTS | 12 | ALDYYDYDFAY | 27 |
| 2.38 | GFSLSNWGVH | 6 | VIWSGGNTDYNTPFDS | 14 | ALDYYDYDFAY | 27 |
| 2.64 | GFSLSNWAVH | 8 | VIWSGGATDYNTPFTS | 12 | ALDYYDYDFAY | 27 |
| 2.69 | GFSLSNWDVH | 9 | VIWSGGNTDYNTPFAS | 16 | ALDYYDYNFAY | 26 |
| 2.80 | GFSLSNWDVH | 9 | VIWSGGNTDYNTPFTS | 11 | ALDYYDYEFAY | 25 |
| 2.85 | GFSLSNWAVH | 8 | VIWSGGNTDYNTPFTS | 11 | ALDYYDYNFAY | 26 |
| 2.87 | GFSLSNWDVH | 9 | VIWSGGATDYNTPFNS | 17 | ALDYYDYNFAY | 26 |
| 2.88 | GFSLSNWDVH | 9 | VIWSGGNTDYNTPFTS | 11 | ALDYYDYEFAY | 25 |
| 2.91 | GFSLSNWGVH | 6 | VIWSGGNTDYNTPFTS | 11 | ALDYYDYNFAY | 26 |
| 2.II.3 | GFSLSNWDVH | 9 | VIWSGGNTDYNTPFTS | 11 | ALDYYDYDFAY | 27 |
| 2.II.10 | GFSLSNWDVH | 9 | VIWSGGNTDYNTPFTS | 11 | ALDYYDYNFAY | 26 |
| Hu 4-59 | GFSLTNYGVH | 1 | VIWSGGNTDYNTPFTS | 11 | ALDYYDYEFAY | 25 |
| 4-59.1 | GFSLTNWGVH | 2 | VIWSGGNTDYNTPFTS | 11 | ALDYYDYEFAY | 25 |
| 4-59.2 | GFSLTNYDVH | 3 | VIWSGGNTDYNTPFTS | 11 | ALDYYDYEFAY | 25 |
| 4-59.3 | GFSLTNYGVH | 1 | NIWSGGNTDYNTPFTS | 18 | ALDYYDYEFAY | 25 |
| 4-59.4 | GFSLTNYGVH | 1 | VIWSGGATDYNTPFTS | 12 | ALDYYDYEFAY | 25 |
| 4-59.5 | GFSLTNYGVH | 1 | VIWSGGTTDYNTPFTS | 19 | ALDYYDYEFAY | 25 |
| 4-59.6 | GFSLTNYGVH | 1 | VIWSGGNPDYNTPFTS | 20 | ALDYYDYEFAY | 25 |
| 4-59.7 | GFSLTNYGVH | 1 | VIWSGGNTDYNTPFTS | 11 | ALDYYDYDFAY | 27 |
| 4-59.8 | GFSLTNYGVH | 1 | VIWSGGNTDYNTPFTS | 11 | ALDYYDYEYAY | 28 |
| 4-59.9 | GFSLTNYGVH | 1 | VIWSGGNTDYNTPFTS | 11 | ALDYYDYEFAY | 25 |
| 4-59.10 | GFSLTNYGVH | 1 | VIWSGGNTDYNTPFTS | 11 | ALDYYDYEFAY | 25 |
| 4-59.11 | GFSLTNYGVH | 1 | VIWSGGNTDYNTPFTS | 11 | ALDYYDYEFAY | 25 |
| 4-59.12 | GFSLTNYGVH | 1 | VIWSGGNTDYNTPFTS | 11 | ALDYYDYEFAY | 25 |
| 4-59.13 | GFSLTNYGVH | 1 | VIWSGGNTDYNTPFTS | 11 | ALDYYDYEFAY | 25 |
| 4.1 | GFSLTNYGVH | 1 | VIWSGGATDYNTPFTS | 12 | ALDYYDYDYAY | 29 |
| 4.2 | GFSLTNWDVH | 10 | NIWSGGTPDYNTPFTS | 21 | ALDYYDYDFAY | 27 |

TABLE 1-continued

CDR Sequences - Heavy Chain Variable Region (HCVR)

| Fab | HCDR1 | SEQ ID NO. | HCDR2 | SEQ ID NO. | HCDR3 | SEQ ID NO. |
|---|---|---|---|---|---|---|
| 4.3 | GFSLTNWGVH | 2 | VIWSGGATDYNTPFTS | 12 | ALDYYDYEYAY | 28 |
| 4.4 | GFSLTNWDVH | 10 | VIWSGGATDYNTPFTS | 12 | ALDYYDYDFAY | 27 |
| 4.5 | GFSLTNYGVH | 1 | NIWSGGTPDYNTPFTS | 21 | ALDYYDYDFAY | 27 |
| 4.7 | GFSLTNWDVH | 10 | NIWSGGNTDYNTPFTS | 18 | ALDYYDYDYAY | 29 |
| 4.8 | GFSLTNWDVH | 10 | NIWSGGNTDYNTPFTS | 18 | ALDYYDYDFAY | 27 |
| 4.9 | GFSLTNWDVH | 10 | NIWSGGAFDYNTPFTS | 22 | ALDYYDYDFAY | 27 |
| 4.11 | GFSLTNYGVH | 1 | NIWSGGTPDYNTPFTS | 21 | ALDYYDYDYAY | 29 |
| 4.12 | GFSLTNYGVH | 1 | NIWSGGTPDYNTPFTS | 21 | ALDYYDYDYAY | 29 |
| 4.13 | GFSLTNWDVH | 10 | VIWSGGTTDYNTPFTS | 19 | ALDYYDYDFAY | 27 |
| 4.14 | GFSLTNWDVH | 10 | NIWSGGNTDYNTFFTS | 18 | ALDYYDYDYAY | 29 |
| 4.15 | GFSLTNYGVH | 1 | NIWSGGNTDYNTPFTS | 18 | ALDYYDYDYAY | 29 |
| 4.16 | GFSLTNWGVH | 2 | NIWSGGNFDYNTPFTS | 23 | ALDYYDYDFAY | 27 |
| 4.17 | GFSLTNYGVH | 1 | NIWSGGNFDYNTPFTS | 23 | ALDYYDYDYAY | 29 |
| 4.18 | GFSLTNYDVH | 3 | VIWSGGNPDYNTPFTS | 20 | ALDYYDYDFAY | 27 |
| 4.19 | GFSLTNWGVH | 2 | VIWSGGTTDYNTPFTS | 19 | ALDYYDYDFAY | 27 |
| 4.21 | GFSLTNWDVH | 10 | VIWSGGNTDYNTPFTS | 11 | ALDYYDYDFAY | 27 |
| 4.22 | GFSLTNYGVH | 1 | NIWSGGNTDYNTPFTS | 18 | ALDYYDYDYAY | 29 |
| 4.23 | GFSLTNWDVH | 10 | NIWSGGNTDYNTFFTS | 18 | ALDYYDYDFAY | 27 |
| Consensus | GFSLX$_5$NX$_7$X$_8$VH<br>X$_5$:T or 8<br>X$_7$:Y or W<br>X$_8$:G, E, D or A | 43 | X$_1$IWSSGGX$_7$X$_8$DYNTPFX$_{15}$S<br>X$_1$:V or N<br>X$_7$:N, A, S or T<br>X$_8$:T or P<br>X$_{15}$:T, D, A or N | 44 | ALX$_3$YYDYX$_8$X$_9$AY<br>X$_3$:T or D<br>X$_8$:E, N or D<br>X$_9$:F or Y | 45 |

TABLE 2

CDR Sequences Light Chain Variable Region (LCVR)

| Fab | LCDR1 | SEQ ID NO. | LCDR2 | SEQ ID NO. | LCDR3 | SEQ ID NO. |
|---|---|---|---|---|---|---|
| Hu 2-26 | RASQSIGTNIH | 30 | YASESIS | 35 | QQNNNWPTS | 37 |
| 2-26.1 | RASQSIGTNIH | 30 | YASESIS | 35 | QQNNNWPTS | 37 |
| 2-26.2 | RASQSIGTNIH | 30 | YASESIS | 35 | QQNNNWPTS | 37 |
| 2-26.3 | RASQSIGTNIH | 30 | YASESIS | 35 | QQNNNWPTS | 37 |
| 2-26.4 | RASQSIGTNIH | 30 | YASESIS | 35 | QQNNNWPTS | 37 |
| 2-26.5 | RASQSIGTNIH | 30 | YASESIS | 35 | QQNNNWPTS | 37 |
| 2-26.6 | RASQSIGTNIH | 30 | YASESIS | 35 | QQNNNWPTS | 37 |
| 2-26.7 | RASQSIGTNIH | 30 | YASESIS | 35 | QQNNNWPTS | 37 |
| 2-26.8 | RASQSIGTNIH | 30 | YASESIS | 35 | QQNNNWPTS | 37 |

TABLE 2-continued

| CDR Sequences Light Chain Variable Region (LCVR) | | | | | | |
|---|---|---|---|---|---|---|
| Fab | LCDR1 | SEQ ID NO. | LCDR2 | SEQ ID NO. | LCDR3 | SEQ ID NO. |
| 2-26.9 | RASQSIGTNIH | 30 | YASESIS | 35 | QQNNNWPTS | 37 |
| 2-26.10 | RASQSIGTNIH | 30 | YASESIS | 35 | QQNNNWPTS | 37 |
| 2-26.11 | RASESIGTNIH | 31 | YASESIS | 35 | QQNNNWPTS | 37 |
| 2-26.12 | RASFSIGTNIH | 32 | YASESIS | 35 | QQNNNWPTS | 37 |
| 2-26.13 | RASYSIOTNIN | 33 | YASESIS | 35 | QQNNNWPTS | 37 |
| 2-26.14 | RASQSIGTNIH | 30 | YASESIS | 35 | QQNNDWPTS | 38 |
| 2-26.15 | RASQSIGTNIH | 30 | YASESIS | 35 | QQNNEWPTS | 39 |
| 2.21 | RASYSIGTNIH | 33 | YASESIS | 35 | QQNNNWPTS | 37 |
| 2.33 | RASESIGTNIH | 31 | YASESIS | 35 | QQNNKWPTS | 40 |
| 2.38 | RASYSIGTNIH | 33 | YASESIS | 35 | QQNNEWPTS | 39 |
| 2.64 | RASYSIGTNIH | 33 | YASESIS | 35 | QQNNNWPTT | 36 |
| 2.69 | RASYSIGTNIH | 33 | YASESIS | 35 | QQNNNWPTS | 37 |
| 2.80 | RASYSIGTNIH | 33 | YASESIS | 35 | QQNNEWPTT | 41 |
| 2.85 | RASYSIGTNIH | 33 | YASESIS | 35 | QQNNDWPTT | 42 |
| 2.87 | RASYSIGTNIH | 33 | YASESIS | 35 | QQNNNWPTT | 36 |
| 2.88 | RASYSIGTNIH | 33 | YASESIS | 35 | QQNNEWPTT | 41 |
| 2.91 | RASESIGTNIH | 31 | YASESIS | 35 | QQNNEWPTS | 39 |
| 2.II.3 | RASYSIGTNIH | 33 | YASESIS | 35 | QQNNDWPTT | 42 |
| 2.II.10 | RASYSIGTNIH | 33 | YASESIS | 35 | QQNNDWPTT | 42 |
| Hu 4-59 | RASQSIGTNIH | 30 | YASESIS | 35 | QQNNDWPTT | 42 |
| 4-59.1 | RASQSIGTNIH | 30 | YASESIS | 35 | QQNNDWPTT | 42 |
| 4-59.2 | RASQSIGTNIH | 30 | YASESIS | 35 | QQNNDWPTT | 42 |
| 4-59.3 | RASQSIGTNIH | 30 | YASESIS | 35 | QQNNDWPTT | 42 |
| 4-59.4 | RASQSIGTNIH | 30 | YASESIS | 35 | QQNNDWPTT | 42 |
| 4-59.5 | RASQSIGTNIH | 30 | YASESIS | 35 | QQNNDWPTT | 42 |
| 4-59.6 | RASQSIGTNIH | 30 | YASESIS | 35 | QQNNDWPTT | 42 |
| 4-59.7 | RASQSIGTNIH | 30 | YASESIS | 35 | QQNNDWPTT | 42 |
| 4-59.8 | RASQSIGTNIH | 30 | YASESIS | 35 | QQNNDWPTT | 42 |
| 4-59.9 | RASHSIGTNIH | 34 | YASESIS | 35 | QQNNDWPTT | 42 |
| 4-59.10 | RASYSIGTNIH | 33 | YASESIS | 35 | QQNNDWPTT | 42 |
| 4-59.11 | RASQSIGTNIH | 30 | YASESIS | 35 | QQNNDWPTT | 42 |
| 4-59.12 | RASQSIGTNIH | 30 | YASESIS | 35 | QQNNEWPTT | 41 |
| 4-59.13 | RASQSIGTNIH | 30 | YASESIS | 35 | QQNNDWPTS | 38 |
| 4.1 | RASYSIGTNIH | 33 | YASESIS | 35 | QQNNDWPTT | 36 |
| 4.2 | RASHSIGTNIH | 34 | YASESIS | 35 | QQNNEWPTS | 37 |
| 4.3 | RASHSIGTNIH | 34 | YASESIS | 35 | QQNNDWPTS | 37 |
| 4.4 | RASQSIGTNIH | 30 | YASESIS | 35 | QQNNDWPTS | 37 |

TABLE 2-continued

CDR Sequences Light Chain Variable Region (LCVR)

| Fab | LCDR1 | SEQ ID NO. | LCDR2 | SEQ ID NO. | LCDR3 | SEQ ID NO. |
|---|---|---|---|---|---|---|
| 4.5 | RASHSIGTNIH | 34 | YASESIS | 35 | QQNNDWPTS | 37 |
| 4.7 | RASYSIGTNIH | 33 | YASESIS | 35 | QQNNDWPTT | 36 |
| 4.8 | RASQSIGTNIH | 30 | YASESIS | 35 | QQNNEWPTS | 37 |
| 4.9 | RASYSIGTNIH | 33 | YASESIS | 35 | QQNNDWPTT | 36 |
| 4.11 | RASYSIGTNIH | 33 | YASESIS | 35 | QQNNNWPTS | 37 |
| 4.12 | RASYSIGTNIH | 33 | YASESIS | 35 | QQNNNWPTS | 37 |
| 4.13 | RASHSIGTNIH | 34 | YASESIS | 35 | QQNNEWPTS | 37 |
| 4.14 | RASYSIGTNIH | 33 | YASESIS | 35 | QQNNDWPTT | 36 |
| 4.15 | RASYSIGTNIH | 33 | YASESIS | 35 | QQNNEWPTS | 37 |
| 4.16 | RASYTGTNIH | 33 | YASESIS | 35 | QQNNDWPTT | 36 |
| 4.17 | RASYSIGTNIH | 33 | YASESIS | 35 | QQNNDWPTT | 36 |
| 4.18 | RASQSIGTNIH | 30 | YASESIS | 35 | QQNNDWPTT | 36 |
| 4.19 | RASYSIGTNIH | 33 | YASESIS | 35 | QQNNDWPTS | 37 |
| 4.21 | RASYSIGTNIH | 33 | YASESIS | 35 | QQNNDWPTS | 37 |
| 4.22 | RASQSIGTNIH | 30 | YASESIS | 35 | QQNNEWPTT | 36 |
| 4.23 | RASQSIGTNIH | 30 | YASESIS | 35 | QQNNEWPTS | 37 |
| Consensus | RASX$_4$SIGTNIH X$_4$:Q, E, F, Y or H | 46 | YASESIS | 35 | QQNNX$_5$WPTX$_9$ X$_5$:N, D, E, or K X$_9$:T or S | 47 |

Each of the Fabs listed in Tables 1 and 2 have been demonstrated to bind to EGFR, as determined by a capture filter lift assay (Example 3) and a capture ELISA (Example 4). The capture ELISA further indicated that each of these Fabs have a greater affinity for EGFR than does chimeric antibody C225.

The structure comprising a CDR of the invention will generally be an antibody heavy or light chain sequence or a substantial portion thereof, in which the CDR is located at a location corresponding to the CDR of a naturally occurring HCVR and LCVR (Kabat et al, Sequences of Proteins of Immunological Interest, US Dept of HHS, 1991). The three CDR regions for each chain, light and heavy, are provided in a framework region as a contiguous sequence represented by the following formula: FR1-CDR1-FR2-CDR2-FR3-CDR3-FR4. The heavy chain or light chain FR1, FR2, FR3 and FR4 combine to form the complete framework when arranged as a contiguous sequence with the CDRs in the order stated. Preferably the framework regions of an antibody of the invention are human, humanized or substantially of human origin.

The antibodies of the present invention represented by different Fabs, the CDRs of which are listed in Tables 1 and 2, differ from each other by sequence changes in at least 1 CDR, and up to as many as 5 CDRs. The differences in CDRs among the clones is indicative that the CDRs for a given position may be substituted for one another, such that a resultant substituted antibody likely retains the ability to bind EGFR and inhibit its activation. In one embodiment of the invention, an antibody comprises a HCVR comprising a CDRH1 comprising a sequence selected from the group consisting of SEQ ID NOS: 1-10 and 43, and/or a CDRH2 comprising a sequence selected from the group consisting of SEQ ID NOS:11-23 and 44, and/or a CDRH3 comprising a sequence selected from the group consisting of SEQ ID NOS:25-29 and 45. In another embodiment, an anti-EGFR antibody of the invention comprises a LCVR comprising a CDRL1 comprising a sequence selected from the group consisting of SEQ ID NOS:30-34 and 46, and/or a CDRL2 comprising the sequence of SEQ ID NO:35, and/or a CDRL3 comprising a sequence selected from the group consisting of SEQ ID NOS:36-42 and 47. In a preferred embodiment, an antibody of the invention comprises a CDRH1 comprising a sequence selected from the group consisting of SEQ ID NOS:1-10 and 43, and/or a CDRH2 comprising a sequence selected from the group consisting of SEQ ID NOS:11-23 and 44, and/or a CDRH3 comprising the sequence of SEQ ID NOS:25-29 and 45, and further comprises a LCVR comprising a CDRL1 comprising a sequence selected from the group consisting of SEQ ID NOS:30-34 and 46, and/or a CDRL2 comprising the sequence of SEQ ID NO:35, and/or a CDRL3 comprising a sequence selected from the group consisting of SEQ ID NOS: 36-42 and 47.

In a preferred embodiment, an anti-EGFR antibody of the present invention has a heavy chain variable region containing the CDRs from one combination of CDRs listed in Table 1, and a light chain variable region containing the CDRs from one combination of CDRs listed in Table 2. Preferably, these HCVRs and LCVRs contain the frameworks as described for the CDRs in Tables 1 and 2. More preferably, a particular antibody has a HCVR containing the CDRs of one of the combination of CDRs listed in Table 1, and a LCVR containing the CDRs of the corresponding combination of CDRs listed in Table 2, e.g., an antibody comprising HCDR1 with SEQ ID NO:1, HCDR2 with SEQ ID NO: 11, HCDR3 with SEQ ID NO: 25, LCDR1 with SEQ ID NO: 30, LCDR2 with SEQ ID NO: 35 and LCDR3 with SEQ ID NO: 37. Preferably, these HCVRs and LCVRs contain the frameworks as described for those particular combinations of CDRs listed in Tables 1 and 2.

In another preferred embodiment, an anti-EGFR antibody of the present invention has a HCVR selected from one of the humanized Fabs listed in Table 3 and LCVR selected from one of the humanized Fabs listed in Table 3. More preferably, the HCVR and LCVR are from the same humanized Fab.

Table 3 presents preferred HCVRs and LCVRs of the antibodies of present invention. The CDR regions are in bold. These HCVRs and LCVRs also present preferred framework regions of the antibodies of the present invention. Antibodies 2.38 through 2.11.3 in Table 3 have framework sequences FRH1 (SEQ ID NO:57), FRH2 (SEQ ID NO:58), FRH3 (SEQ ID NO:59), and FRH4 (SEQ ID NO:60) which are from the VH2-26 human germline framework. Likewise, this is the preferred framework for antibodies Hu 2-26 through 2.II.10 in Table 1. Antibodies 4.14 through 4.21 in Table 3 have frameworks FRH1 (SEQ ID NO:61), FRH2 (SEQ ID NO:62), FRH3 (SEQ ID NO:63), and FRH4 (SEQ ID NO:64) which are from the VH 4-59 human germline framework. Likewise, this is the preferred framework for antibodies Hu 4-59 through 4.23 in Table 1. All of the antibodies in Table 3 have frameworks FRL1 (SEQ ID NO:74), FRL2 (SEQ ID NO:75), FRL3 (SEQ ID NO:76), and FRL4 (SEQ ID NO:77) from the VK A26 human germline framework, which is also the preferred framework for antibodies Hu-2-26 through 4.23 in Table 2.

TABLE 3

Humanized Heavy Chain Variable Regions (VH2-26 and VH4-59 Templates)

```
                              HCDR1                             HCDR2
2.38     QVTLKESGPVLVKPTETLTLTCTVSGFSLSNWGVHWIRQPPGKALEWLAVIWSGGNTDYNTPFDS
2.69     QVTLKESGPVLVKPTETLTLTCTVSGFSLSNWDVHWIRQPPGKALEWLAVIWSGGNTDYNTPFAS
2.87     QVTLKESGPVLVKPTETLTLTCTVSGFSLSNWDVHWIRQPPGKALEWLAVIWSGGATDYNTPFNS
2.88     QVTLKESGPVLVKPTETLTLTCTVSGFSLSNWDVHWIRQPPGKALEWLAVIWSGGNTDYNTPFTS
2.11.3   QVTLKESGPVLVKPTETLTLTCTVSGFSLSNWDVHWIRQPPGKALEWLAVIWSGGNTDYNTPFTS
              FRH1                              FRH2
           (SEQ ID NO:57)                    (SEQ ID NO:58)

4.14     QVQLQESGPGLVKPSETLSLTCTVSGFSLTNWDVHWIRQPPGKGLEWIGNIWSGGNTDYNTPFTS
4.15     QVQLQESGPGLVKPSETLSLTCTVSGFSLTNYGVHWIRQPPGKGLEWIGNIWSGGNTDYNTPFTS
4.21     QVQLQESGPGLVKPSETLSLTCTVSGFSLTNWDVHWIRQPPGKGLEWIGVIWSGGNTDYNTPFTS
              FRH1                              FRH2
           (SEQ ID NO:61)                    (SEQ ID NO:62)
```

|  |  | SEQ ID No: |
|---|---|---|
| | HCDR3 | |
| 2.38 | RLTISKDTSKSQVVLTMTNMDPVDTATYYCARALDYYDYDFAYWGQGTMVTVSS | 49 |
| 2.69 | RLTISKDTSKSQVVLTMTNMDPVDTATYYCARALDYYDYNFAYWGQGTMVTVSS | 50 |
| 2.87 | RLTISKDTSKSQVVLTMTNMDPVDTATYYCARALDYYDYNFAYWGQGTMVTVSS | 51 |
| 2.88 | RLTISKDTSKSQVVLTMTNMDPVDTATYYCARALDYYDYEFAYWGQGTMVTVSS | 52 |
| 2.11.3 | RLTISKDTSKSQVVLTMTNMDPVDTATYYCARALDYYDYDFAYWGQGTMVTVSS | 53 |
| | FRH3                              FRH4 | |
| | (SEQ ID NO:59)                    (SEQ ID NO:60) | |
| 4.14 | RVTISVDTSKNQFSLKLSSVTAADTAVYYCARALDYYDYDYAYWGQGTMVTVSS | 54 |
| 4.15 | RVTISVDTSKNQFSLKLSSVTAADTAVYYCARALDYYDYDYAYWGQGTMVTVSS | 55 |
| 4.21 | RVTISVDTSKNQFSLKLSSVTAADTAVYYCARALDYYDYDFAYWGQGTMVTVSS | 56 |
| | FRH3                              FRH4 | |
| | (SEQ ID NO:63)                    (SEQ ID NO:64) | |

Humanized Light Chain Variable Regions (VL A26 Template)

```
                              LCDR1                   LCDR2
2.38     EIVLTQSPDFQSVTPKEKVTITCRASYSIGTNIHWYQQKPDQSPKLLIKYASESIS
2.69     EIVLTQSPDFQSVTPKEKVTITCRASYSIGTNIHWYQQKPDQSPKLLIKYASESIS
2.87     EIVLTQSPDFQSVTPKEKVTITCRASYSIGTNIHWYQQKPDQSPKLLIKYASESIS
2.88     EIVLTQSPDFQSVTPKEKVTITCRASYSIGTNIHWYQQKPDQSPKLLIKYASESIS
2.II.3   EIVLTQSPDFQSVTPKEKVTITCRASYSIGTNIHWYQQKPDQSPKLLIKYASESIS
4.14     EIVLTQSPDFQSVTPKEKVTITCRASYSIGTNIHWYQQKPDQSPKLLIKYASESIS
4.15     EIVLTQSPDFQSVTPKEKVTITCRASYSIGTNIHWYQQKPDQSPKLLIKYASESIS
4.21     EIVLTQSPDFQSVTPKEKVTITCRASYSIGTNIHWYQQKPDQSPKLLIKYASESIS
              FRL1                    FRL2
           (SEQ ID NO:74)          (SEQ ID NO:75)
```

SEQ ID NO:

LCDR3

TABLE 3-continued

| | | |
|---|---|---|
| 2.38 | GVPSRFSGSGSGTDFTLTINSLEAEDAATYYCQQNNEWPTSFGGGTKVEIK | 66 |
| 2.69 | GVPSRFSGSGSGTDFTLTINSLEAEDAATYYCQQNNNWPTSFGGGTKVEIK | 67 |
| 2.87 | GVPSRFSGSGSGTDFTLTINSLEAEDAATYYCQQNNNWPTTFGGGTKVEIK | 68 |
| 2.88 | GVPSRFSGSGSGTDFTLTINsLEAEDAATYYCQQNNEWPTSFGGGTKVEIK | 69 |
| 2.11.3 | GVPSRFSGSGSGTDFTLTINSLEAEDAATYYCQQNNDWPTTFGGGTKVEIK | 70 |
| 4.14 | GVPSRFSGSGSGTDFTLTINSLEAEDAATYYCQQNNDWPTTFGGGTKVEIK | 71 |
| 4.15 | GVPSRFSGSGSGTDFTLTINSLEAEDAATYYCQQNNEWPTSFGGGTKVEIK | 72 |
| 4.21 | GVPSRFSGSGSGTDFTLTINSLEAEDAATYYCQQNNDWPTSFGGGTKVEIK | 73 |
| | FRL3 FRL4 | |
| | (SEQ ID NO:76) (SEQ ID NO:77) | |

In accordance with the invention disclosed herein, antibodies having enhanced ability to inhibit EGFR activation can be generated by combining in a single polypeptide structure one or more novel CDR sequences as disclosed herein. In this manner, several novel amino acid sequences can be combined into one antibody, in the same or different CDRs, to produce antibodies with desirable levels of anti-EGFR activity. Such desirable levels will often result from producing antibodies whose Kd values preferably 1 pM or less. By way of a non-limiting example, such novel CDR sequences, as presented in Tables 1 and 2, may be employed and the resulting antibodies screened for the ability to inhibit EGFR activation, using any or several of the assays as described below in Examples 6-10.

Antibodies of the present invention can be examined for several beneficial properties that contribute to the utility of an antibody for a particular indication. In one embodiment, antibodies of the present invention will have an affinity for EGFR that is greater (i.e., a lower Kd number) than that of antibodies known in the art such as chimeric antibody C225, as determined by Kd, (e.g., Biacore or Kinexa assays). As described above, Kd is measured by the ratio of the $k_{on}$ and $k_{off}$ constants. For example, a $k_{on}$ of $3.1\times10^7$ $(M^{-1}s^{-1})$ and a $k_{off}$ of $0.9\times10^{-4}(s^{-1})$ would combine to give a Kd of $2.9\times10^{-12}M$. Thus, affinity can be improved by increasing the $k_{on}$ or decreasing the $k_{off}$.

Improvements in anti-EGFR antibody affinity may well correspond with an enhanced ability of an antibody to inhibit EGFR activation. Aspects of enhanced ability to inhibit EGFR activation may be examined through any of several in vitro and in vivo assays, as described in Examples 6-10. These assays include, but are not limited to, a cell proliferation assay, an apoptosis assay, a receptor binding assay, a receptor phosphorylation assay, or a mouse tumor model. Preferably, antibodies of the present invention will have improved ability to inhibit EGFR activation as determined by any or several of these assays. More preferably, antibodies of the present invention will have a Kd no greater than 10 pM, more preferably no greater than 1 pM and even more preferably no greater than about 0.2 pM, and have enhanced ability to inhibit activation of EGFR.

Antibody Expression

In another aspect, the present invention also is directed to recombinant DNA encoding the antibodies and fragments of the invention. The sequence of recombinant DNA encoding an antibody or fragment of the invention can be readily determined by one of skill in the art using the genetic code. A nucleic acid having the determined sequence can be prepared and expressed in any of a wide variety of host systems using techniques that are well known in the art.

Preferably, the DNA encodes antibodies that, when expressed, comprise one to five of the light and heavy chain CDRs of SEQ ID NOS:1, 11, 24, 30, 35, 36, and one or more of the light and heavy chain CDRs of SEQ ID NOS:2-10, 12-23, 25-29, 31-34, 37-42, for a total of 6 CDRs (CDRH1, CDRH2, CDRH3, CDRL1, CDRL2, CDRL3, wherein CDRL2 will be SEQ ID NO:35). In addition, the DNA preferably encodes antibodies that, when expressed, comprise these CDRs in combination with the preferred light chain and heavy chain frameworks of the present invention, as depicted in the sequences shown in Table 3.

DNA encoding the antibodies of the present invention will typically further include an expression control polynucleotide sequence operably linked to the antibody coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired antibodies can be formed from a variety of different polynucleotides (genomic or cDNA, RNA, synthetic oligonucleotides, etc.) and components (e.g., V, J, D, and C regions), using any of a variety of well known techniques. Joining appropriate genomic and synthetic sequences is a common method of production, but cDNA sequences may also be utilized.

Human constant region DNA sequences can be isolated in accordance with well known procedures from a variety of human cells, but preferably from immortalized B-cells. Suitable source cells for the polynucleotide sequences and host cells for immunoglobulin expression and secretion can be obtained from a number of sources well-known in the art.

As described herein, in addition to the antibodies specifically described herein, other modified antibodies having sequence substantially similar or identical sequences can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in vectors using site-directed mutagenesis, such as after CH1 to produce Fab fragments or after the hinge region to produce F(ab')$_2$ fragments. Single chain antibodies may be produced by joining VL and VH with a DNA linker.

As stated previously, the polynucleotides will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

*E. coli* is a prokaryotic host useful particularly for cloning the polynucleotides of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Pichia pastoris* is a preferred host, with suitable vectors having expression control sequences, such as promoters, including 3-phosphoglycerate kinase or other glycolytic enzymes, and an origin of replication, termination sequences and the like as desired.

Mammalian tissue cell culture may also be used to express and produce the polypeptides of the present invention. Eukaryotic cells are preferred, because a number of suitable host cell lines capable of secreting intact immunoglobulins have been developed in the art, and include the CHO cell lines, various COS cell lines, HeLa cells, myeloma cell lines, transformed B-cells, human embryonic kidney cell lines, or hybridomas. Preferred cell lines are CHO and myeloma cell lines such as SP2/0 and NS0.

Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. Preferred polyadenylation sites include sequences derived from SV40 and bovine growth hormone.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Once expressed, the antibodies can be purified according to standard procedures, including ammonium sulfate precipitation, ion exchange, affinity (e.g. Protein A), reverse phase, hydrophobic interaction column chromatography, gel electrophoresis, and the like. Substantially pure immunoglobulins having at least about 90 to 95% purity are preferred, and 98 to 99% or more purity most preferred, for pharmaceutical uses. Once purified, partially or to homogeneity as desired, the polypeptides may then be used therapeutically or prophylactically, as directed herein.

Therapeutic Use for the Antibody

This invention also relates to a method of treating humans experiencing an EGFR mediated cancer which comprises administering an effective dose of an antibody that binds to EGFR to a patient in need thereof. The antibodies of the present invention bind to EGFR and inhibit is activation. Various EGFR-mediated cancers include but are not limited to non-small cell lung cancer, breast cancer, colorectal cancer, head and neck cancers, and prostate cancer.

The antibodies, or antigen binding portions thereof, of the present invention can be in the form of a composition comprising the antibody of the invention suspended in a pharmacologically acceptable diluent or excipient. These pharmaceutical compositions may be administered by any means known in the art that achieve the generally intended purpose to treat autoimmune diseases, preferably multiple sclerosis. The preferred route of administration is parenteral, defined herein as referring to modes of administration that include intravenous, intramuscular, intraperitoneal, intrasternal, subcutaneous, and intraarticular injection and infusion. The dosage administered will be dependent upon the age, health, and weight of the recipient, kind of concurrent treatment, if any, frequency of treatment, and the nature of the effect desired.

Compositions within the scope of the invention include all compositions wherein an antibody or antigen binding portion is present in an amount that is effective to achieve the desired medical effect for treating cancer.

The pharmaceutical compositions for administration are designed to be appropriate for the selected mode of administration, and pharmaceutically acceptable excipients such as, buffers, surfactants, preservatives, solubilizing agents, isotonicity agents, stabilizing agents and the like are used as appropriate. *Remington's Pharmaceutical Sciences*, Mack Publishing Co., Easton Pa., latest edition, provides a compendium of formulation techniques as are generally known to practitioners.

The concentration of the anti-EGFR antibody in formulations may be from as low as about 0.1% to as much as 15 or 20% by weight and will be selected primarily based on fluid volumes, viscosities, stability, and so forth, in accordance with the particular mode of administration selected. Preferred concentrations of the anti-EGFR antibody will generally be in the range of 1 to about 100 mg/mL. Preferably, 10 to about 50 mg/mL.

The formulation may be sterile filtered after making the formulation, or otherwise made microbiologically acceptable. A preservative such as m-cresol or phenol, or a mixture thereof may be added to prevent microbial growth and contamination.

A typical composition for intravenous infusion could have a volume as much as 250 mL of fluid, such as sterile Ringer's solution, and 1-100 mg per mL, or more in antibody concentration. Therapeutic agents of the invention can be frozen or lyophilized for storage and reconstituted in a suitable sterile carrier prior to use. Lyophilization and reconstitution can lead to varying degrees of antibody activity loss (e.g., with conventional immunoglobulins, IgM antibodies tend to have greater activity loss than IgG antibodies). Dosages may have to be adjusted to compensate.

Although the foregoing methods appear to be the most convenient and most appropriate for administration of proteins such as humanized antibodies, by suitable adaptation, other techniques for administration, such as transdermal administration and oral administration may be employed provided proper formulation is designed. In addition, it may be desirable to employ controlled release formulations using biodegradable films and matrices, or osmotic mini-pumps, or delivery systems based on dextran beads, alginate, or collagen.

Typical dosage levels can be optimized using standard clinical techniques and will be dependent on the mode of administration and the condition of the patient. Generally, doses will be in the range of 10 µg/kg/month to 10 mg/kg/month.

In another aspect, the antibodies or antigen binding portions thereof of the present invention for use as a medicament for the treatment of cancer is contemplated.

In yet another aspect, an article of manufacture such as a container, a package, packaging material, dispenser, and the like, is contemplated.

The invention is illustrated by the following examples that are not intended to be limiting in any way.

EXAMPLES

Example 1

Cloning and Expression of a Soluble EGFR (sEGFR)

Human EGFR consists of a single polypeptide chain containing extracellular, transmembrane and intracellular regions. To provide soluble antigen for use, for example, in binding assays, the extracellular region is cloned and expressed as follows.

Primers are designed based on the sequence of the human EGFR to isolate the first 643 amino acids of the precursor protein by RT-PCR. The upstream "sense" primer (Primer 3053) adds a Kpn I site for cloning and alters the Kozak sequence and the first amino acid of the signal sequence to conform to a consensus Kozak sequence and improve eukaryotic expression. The start codon is underlined in each of the sequences presented below.

```
Primer 3053:
                                            [SEQ ID NO:78]
TAA GGT ACC GCT CTT CGG GGA GCC ACC ATG GGA CCC
TCC GGG ACG Native Sequence:
                                            [SEQ ID NO:79]
GCT CTT CGG GGA GCA GCC ATG CGA CCC TCC GGG ACG
```

The downstream "antisense" primer (Primer 3054) terminates the protein at 1619 (based on the amino acid numbering of the mature protein) and added a (Gly)$_4$Ser linker [Gly Gly Gly Gly Ser; SEQ ID NO:80] and a (His)$_6$ tag [SEQ ID NO:81]. An Xba I site is included for cloning.

```
Primer 3054:
                                            [SEQ ID NO:82]
ATG TCT AGA AAC TCA ATG GTG ATG GTG ATG ATG CGA

GCC ACC GCC ACC GAT CTT AGG CCC ATT CGT TGG ACA
```

Figure 2:
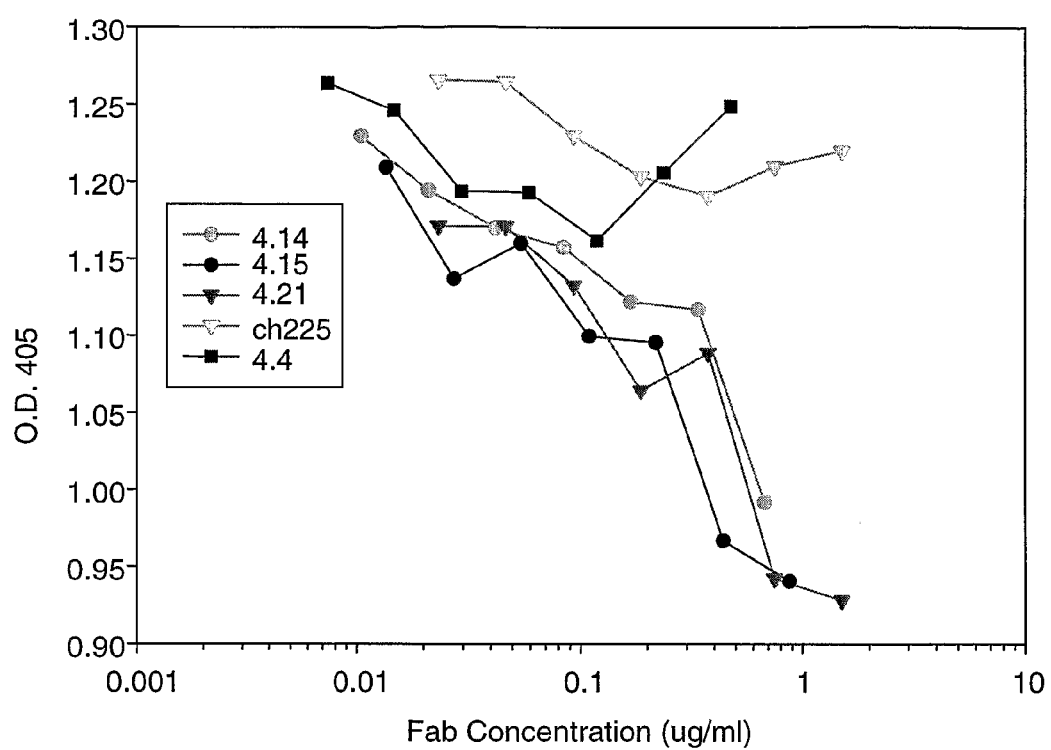
FIG. 2. shows the results of a A431 cell proliferation assay with Fabs 4.14, 4.15, 4.21, 4.4, and chimeric antibody C225.

The amino acid sequence of the mature sEGFR with the fused linker and (His)$_6$ tag [SEQ ID NO: 6] is presented in FIG. 2 mRNA is isolated from human A431 epidermal carcinoma cells (ATCC CRL-1555) using a Fast-Track (Invitrogen) kit. The extracellular portion of the gene is amplified using SuperScript One-step RT-PCR (GibcoBRL) with primers 3053 and 3054 and cloned into the pCRII (Invitrogen) holding vector. The tagged gene segment is confirmed by DNA sequencing and is inserted as an Xba I/Kpn I fragment into the pcDNA 3.1 (Invitrogen) expression vector.

Plasmid DNA is linearized and electroporated into CHO-K1 cells. Clones are selected for resistance to Geneticin (GibcoBRL). Approximately 100 colony supernatants are tested for expression of soluble EGFR (sEGFR) by western blot developed with m225 (Ab-2) antibody (Lab Vision Corp.). An appropriately expressing clone is expanded, subcloned by limiting dilution and adapted to serum free medium (CHO SFII, GibcoBRL).

The soluble antigen is semi-purified from terminal flask culture supernates by concentration and binding to Ni-NTA Sepharose (Qiagen, Valencia, Calif.). Specifically, the supernatant of terminal cells is harvested by centrifuging to pellet cells, and then the supernatant is filtered to remove any traces of cell debris and subsequently kept at 0-4° C. for remaining purification steps. The supernatant is concentrated to a total of approximately 100 mls using the Amicon concentrator with 30,000 MWCO membrane. The concentrate is dialyzed into Buffer A (Buffer A: 50 mM Sodium Phosphate pH 8.0, 300 mM NaCl, 0.5 mM Imidizole) overnight. The buffer may be changed once if desired. After dialysis, approximately 800 µl Ni-NTA beads are washed 2-3 times with Buffer A, and then are added to dialyzed supernatant in 50 ml conical tubes and rotated in cold room for 2 hours. The beads are spun down in 50 ml conical tubes, and most of the supernatant is transferred to another container leaving a small, manageable amount of supernatant in tubes. This supernatant is vortexed to resuspend beads and beads are loaded onto a suitable commercial column. The liquid is allowed to run through, and then the rest of the supernatant is added to the column. The supernatant is recycled through the column 2-3 times. The column is washed with approximately 10 mls Buffer A. The column is eluted with approximately 3-4 mls Buffer A containing 200 mM Imidizole and 2501 fractions are collected. The OD$_{280}$ of fractions is checked on a plate reader using elution buffer as a blank. The most concentrated fractions are pooled and dialyzed into PBS overnight. The pooled dialyzed fractions can be frozen at −70° C. after the addition of 1/10 volume of glycerol, or the dialyzed fractions can be biotinylated (see below).

The sEGFR was eluted with 500 mM Imidizole and dialyzed into PBS as described above. The mixed protein fraction containing sEGFR was biotinylated using Sulfo-NHS-LC-Biotin (Pierce 21335) and dialyzed against PBS to remove unincorporated reagent. Aliquots of biotinylated sEGFR (B-sEGFR) are stored in 10% glycerol at −80° C.

Example 2

Isolation of Fabs Expressed in Bacteria

Expressed Fabs of the present invention may be isolated from bacterial periplasm as follows. XL-0 cells are grown at 37° C. with 250 rpm shaking in 2×YT medium until an OD 600 nm of approximately 0.9 to 1.2 is reached. IPTG is then added to a final concentration of 1 mM (from a 1 M stock). For each clone to be analyzed, 15 ml of cells are placed in a sterile conical tube. The cells are infected with 10 µl of a high titer phage stock and incubated at 37° C. for one hour with shaking. Cells are transferred to 25° C. and grown overnight with shaking. The cells are pelleted in a tabletop clinical centrifuge at ~2000×g for 25 minutes. The cells are resuspended in 1 ml 30 mM Tris-Cl pH 8.0, 150 mM NaCl by pipetting up and down, then transferred to an eppendorf tube. The samples are pelleted for 3 min at 8000 rpm in a microcentrifuge. The supernatant is aspirated and discarded. The pellet is resuspended in 50 mM Tris-Cl pH 8.0, 150 mM NaCl, 500 mM sucrose, then vortexed and placed on ice for 30 min. The cellular debris is pelleted for 10 min at 9000 rpm in a microcentrifuge at 4° C. The supernatant is isolated and stored at 4° C.

Example 3

Identification of Fabs by Filter Lift

Phage expressed Fabs which bind biotinylated sEGFR are detected from a diverse population of Fabs by Fab filter or capture lifts. ct phage expressed Fabs which bind B-sEGFR, e.g., from a diverse population of phage-expressed Fabs. Briefly, a filter is coated with a capture reagent (goat anti-human kappa chain antibody), then the coated filter is placed on a plate with phage plaques, from phage which are expressing Fabs. The filter is incubated with the plaques, then the filter is incubated with biotinylated sEGFR, and bound biotinylated sEGFR is detected by binding of Neutravidin-AP and incubation with the detectable alkaline phosphatase substrate.

Specifically, a Nitrocellulose (BA85, Schleicher and Schull) filter is coated by floating on 5 mL of goat anti-human kappa (2060-01, Southern Biotech) at 10 µg/mL in PBS for two hours at room temp. The filter is submerged for 15 min. The filter is washed three times in PBS. The filter is blocked in 1% BSA in PBS for 1 hour. The filter is washed three times in PBS. The filter is air dried for 10 min. The filter is carefully laid onto phage plate and incubated overnight at 22° C. The filter is carefully lifted off and washed briefly in PBS. The filter is incubated with Biotinylated antigen at 1/1000 dilution into 3% dry milk, PBS, 0.05% Tween 20 for 1 hour at room temperature. The filter is vacuum washed with PBS, 0.05% Tween 20 three times. The filter is incubated with Neutravidin-AP 1/1000 in PBS, 0.05% Tween 20 for 30 min. at room temperature. The filter is vacuum washed with PBS, 0.05% Tween 20 three times. The filter is developed in 10 mls AP substrate (Nitro-blue tetrazolium, 5-Bromo-4-chloro-indolyl phosphate, Pierce, Rockford, Ill.). Plaques are selected based on blue color intensity.

Example 4

Capture ELISA Assay of Fab Binding sEGFR

Capture ELISA is used as an assay to detect Fabs which bind sEGFR as follows. A Costar U-bottom plate is coated with 50 µL/well goat anti-human Kappa antibody (2060-01 Southern Biotech, Birmingham Ala.) at 10 µg/mL in carbonate buffer (0.015M sodium carbonate, 0.035M sodium bicarbonate, pH 9.5) overnight at 4° C. The wells are washed 3 times with PBS-Tween 20 (0.05%). the wells are blocked with 50 µL/well 1% BSA in PBS-Tween for 1 hour at RT. The wells are washed 3 times with PBS-Tween. 50 µL/well Periprep Fab (see Example 2, diluted to 5 µg/mL in PBS-Tween) with 1:5 dilutions down the plate in duplicate are added. The plate is incubated at RT for 2 hours. The plate is wash 3 times with PBS-Tween. 50 µL/well biotinylated-sEGFR diluted 1/1000 in PBS-Tween are added and the plate is incubated at RT for 1 hour. The plate is washed 3 times with PBS-Tween. 50 µL/well Neutravidin-Alkaline Phosphatase (Neutravidin-AP; Pierce, Rockford, Ill.) diluted 1/1000 in PBS-Tween are added and incubated for 30 min. at RT. The plate is washed 3 times with PBS-Tween. 150 µL/well pNPP substrate (Sigma) is added and incubated at 37° C. until color develops. The plate is read at OD 405.

The results of Fabs assayed for binding to sEGFR by capture are shown in FIG. 1.

Example 5

Assay of Fab Binding to A431 Carcinoma Cell Lysates

Fab binding to EGFR may be assayed with A431 carcinoma cell lysates as follows. A-431 cell lysates are prepared as described in "Purification of an Active EGF Receptor Kinase with Monoclonal Antireceptor Antibodies, Yarden et al, (1985) J. Biol. Chem., 260, 315-319". Briefly, confluent monolayers of A-431 cells are washed twice with PBS and once with HNEG (20 mM Hepes buffer pH 7.5, 150 mM NaCl, 1 mM EGTA, 10% glycerol). The cells are scraped into 20 mL of HNEG and centrifuged 600×g for 10 min. $10^7$ cells are suspended in 1 mL solubilization buffer (50 mM HEPES pH 7.5, 150 mM NaCl, 1% Tritob X-100, 10% glycerol, 1 mM EDTA, 1.5 mM MgCl2, 5 ug/mL leupeptin, 1% Aprotinin) and then homogenized in a glass-glass homogenizer. The insoluble material is removed by centrifugation at 40,000×g for 30 min. The clear supernate was removed and frozen at −80° C.

A Costar U-bottom plate is coated with 50 µL/well cell lysate diluted 1/20 in 10 mM HEPES pH 7.4, 0.1% Triton X-100 and dried in a hood overnight. The plate is blocked by adding 100 µL/well PBS, 0.5% BSA and incubated 1 hour at RT. The plate is washed 3 times with PBS, 0.05% Tween. 50 µl/well of Fab is added, starting at 1-5 µg/ml with 1/5 dilutions in PBS, 0.05% Tween, and incubated for 1 hr at RT. The plate is washed 3 times with PBS-Tween. 100 µL/well of goat anti-human Kappa-AP (2060-01, Southern Biotech Birmingham, Ala.) at 1/2000 in PBS-Tween are added to the wells. The plate is incubated 1 hour at RT. The plate is washed 3 times with PBS-Tween. 150 µL/well pNPP (N-9389, Sigma, Saint Louis, Mo.) substrate [Source/Cat. #] (1 tablet/3 mL water) is added, and incubated at 37° C. for up to 1 hour. The plate is read at OD 405.

Example 6

Inhibition of Cell Proliferation by Anti-EGFR Antibodies

Cell proliferation assays with A431 epidermal carcinoma cells are used to determine the relative potency of anti-EGFR Fabs. The assay is based on previous studies (Sato et al, "Biological Effects in vitro of Monoclonal Antibodies to Human Epidermal Growth Factor Receptors", (1983), Mol. Biol. Med., 1, 511-529) that demonstrate decreased cell-proliferation of A431 cells in response to anti-EGF-receptor antibodies. The cell proliferation assays are as follows. A431 cells are maintained in DMEM plus 10% FBS. On Day 1, cells are placed in PBS for 20 minutes and trypsinized for 5 minutes prior to plating. Cells are plated at a cell density of 15,000 cells per well in 384 well format on Greiner 384 TC treated cell culture plates using a multidrop 384. Final medium volume is 50 μl. Cell culture plates are covered with airpore tape (Qiagen, Valencia, Calif.). Cells are allowed to adhere over night. On Day 2 cell culture medium is removed and replaced with either 50 μl phenol red free DMEM (no FBS) ["control wells"] or DMEM and Fab periplasm prep (see Example 2) ["treatment wells"] in duplicate at an expected concentration of 2.5 μg/ml. Two control wells are located adjacent to each treatment well for a total of 192 control wells. On Day 3, medium is removed and replaced with phenol red free DMEM containing MTS cell proliferation reagent (Promega, Madison, Wis.; 1 ml/10 ml medium). Absorbance at 490 nm is recorded after 15 and 30 minutes. The mean value for all duplicate treatments is divided by the mean for all control wells.

Figure 3:
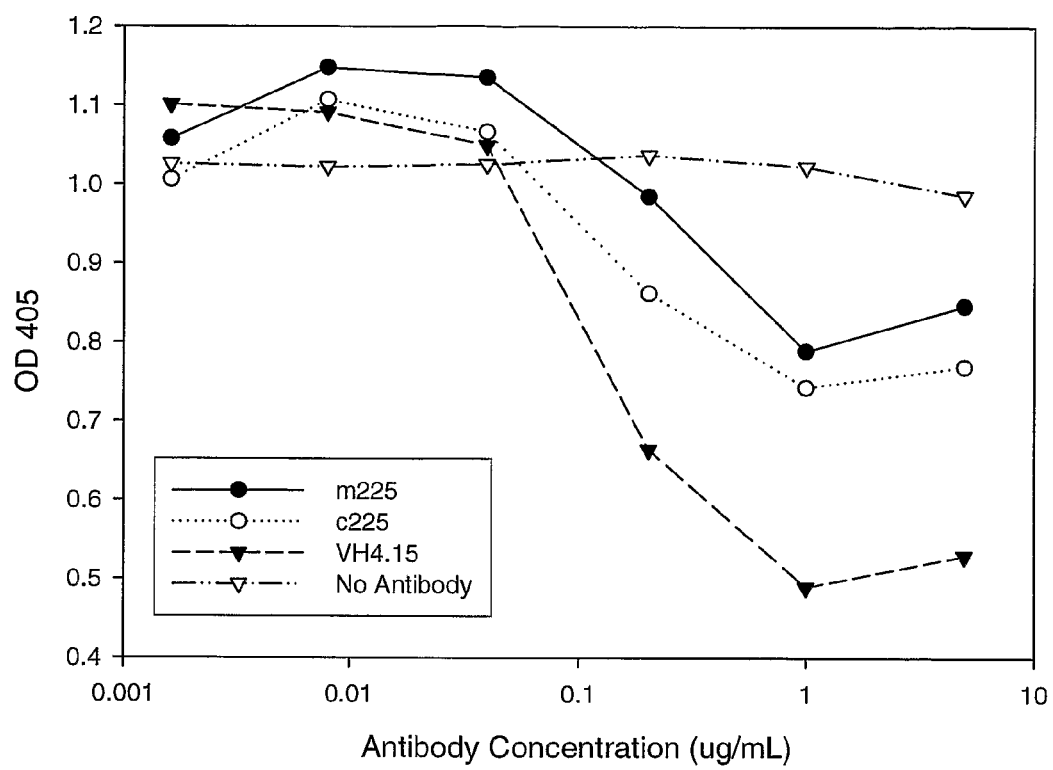
FIG. 3. shows the inhibition of A431 cell proliferation by full-length antibodies 4.15, murine antibody 225, and chimeric antibody C225.

The results of a representative assay with Fabs are shown in FIG. 2. Likewise, the results of a representative assay with full length antibodies is shown in FIG. 3. The data shown in FIGS. 2 and 3 respectively are expressed as the percent of signal obtained when cells are incubated in the absence of Fab or antibody (=100%). It should be noted that a percent signal strength does not necessarily correlate perfectly with actual cell number.

Example 7

Binding Affinity

Binding affinity measurements for full-length monoclonal antibodies of the invention are determined using a Sapidyne KINEXA assay. NHS-activated fast-flow sepharose beads (GE Healthcare) are pre-coated with antigen (50 μg anti-EGFR antibody per ml of beads) and blocked with 10 mg/ml BSA in 1 M Tris-HCl, pH 8.0. Then 2 pM, 4 pM, 40 pM of an antibody of the invention is incubated with various concentration (e.g., 2.4 pM to 10 nM, serial dilutions) of sEGFR in running buffer (PBS, 0.005% (v/v) Tween-20 and 1 mg/ml ovalbumin) for 10 hours at room temperature. To determine the free antibody present at equilibrium, each sample is passed through the sEGFR-coated beads. The amount of bead-bound antibody is then quantified by passing a solution of fluorescent (Cy5) labeled goat anti-human Fc antibody (Jackson Immuno Research) diluted 1:4000 in running buffer over the beads. The measured fluorescence signal is proportional to the concentration of free antibody at equilibrium. Each concentration of sEGFR is measured in duplicate. The equilibrium dissociation constant ($K_D$) is obtained from non-linear regression of the competition curves using a multiple-curve, one-site homogeneous binding model (KINEXA software).

The association rate constant ($k_{on}$) for sEGFR binding is also determined using a Sapidyne KINEXA assay. Two pM antibody is mixed with 20 pM sEGFR using the same conditions as described above. At various times, samples are probed for free antibody using the conditions described above for equilibrium binding, and then the resulting time dependence is fit using the KINEXA software to determine the association rate ($k_{on}$). The dissociation rate constant ($k_{off}$) is calculated using the expression $k_{off}=K_d \times k_{on}$. Affinities of full-length monoclonal antibodies were measured using the described assay, and the results obtained are listed below in Table 4.

TABLE 4

Antibody affinities (measurements performed on KinExA3000 Instrument (Sapidyne))

| Antibody | On Rate | Off Rate | Kd (pM) |
|---|---|---|---|
| C225 | 7.97E+06 | 3.00E−03 | 379 |
| VH2.69 | 9.64E+06 | 6.51E−06 | 0.680 |
| VH2.87 | | | 0.215 |
| VH4.15 | 1.46E+07 | 1.46E−06 | 0.012 |
| VH4.21 | 1.07E+07 | 2.02E−06 | 0.188 |
| ABX-EGF | 2.98E+06 | 1.49E−04 | 50 |

Example 8

Phosphorylation of EGFR

The ability of antibodies of the present invention to inhibit phosphorylation of EGFR is assayed as follows. A431 cells are grown to ~70% confluence in 6-well plates and serum starved overnight in DMEM 0.5% FBS. The cells were then incubated with antibody dilutions in the presence of 100 nM EGF (Upstate) for one hour. Cells were washed with cold PBS and lysed with 0.5 mL lysis buffer. (50 mM Tris-HCl pH 7.4, 1% IGEPGAL CA-630, 0.25% sodium deoxycholate, 150 mM NaCl, 1 mM PMSF, 1 mM sodium vanadate (NaVO4), 1 mM NaF, ½ tablet protease cocktail in 10 mL). Insoluble material was removed by ultracentrifugation at 10,000 RPM for 30 min. Cell lysates were adjusted for protein concentration and equivalent amounts of each extract were separated by SDS-PAGE. Phosphorylated EGFR was determined by Western blot developed with an anti-phospho-EGFR (Upstate).

Figure 4:
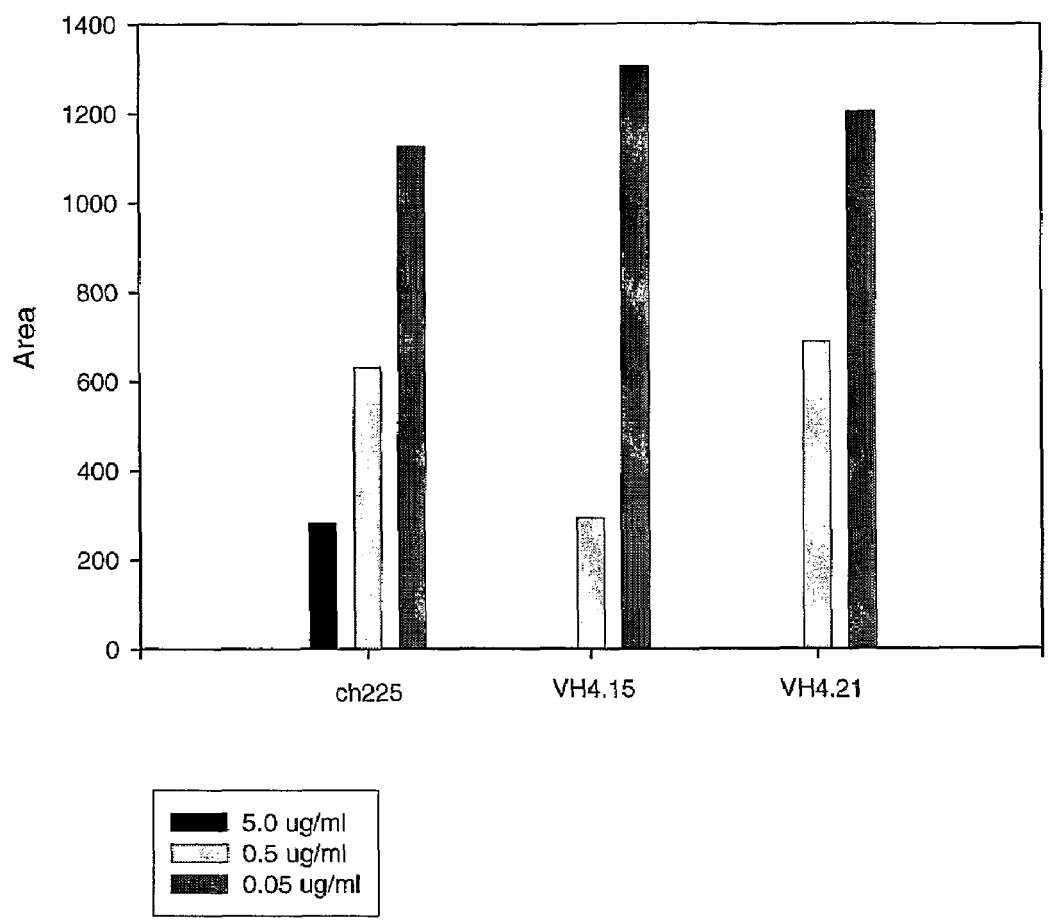
FIG. 4. shows the amount of phosphorylated EGFR (p-Tyr EGFR) detected in A431 cells preincubated with antibodies 4.15, 4.21, or chimeric antibody C225.
Figure 5:
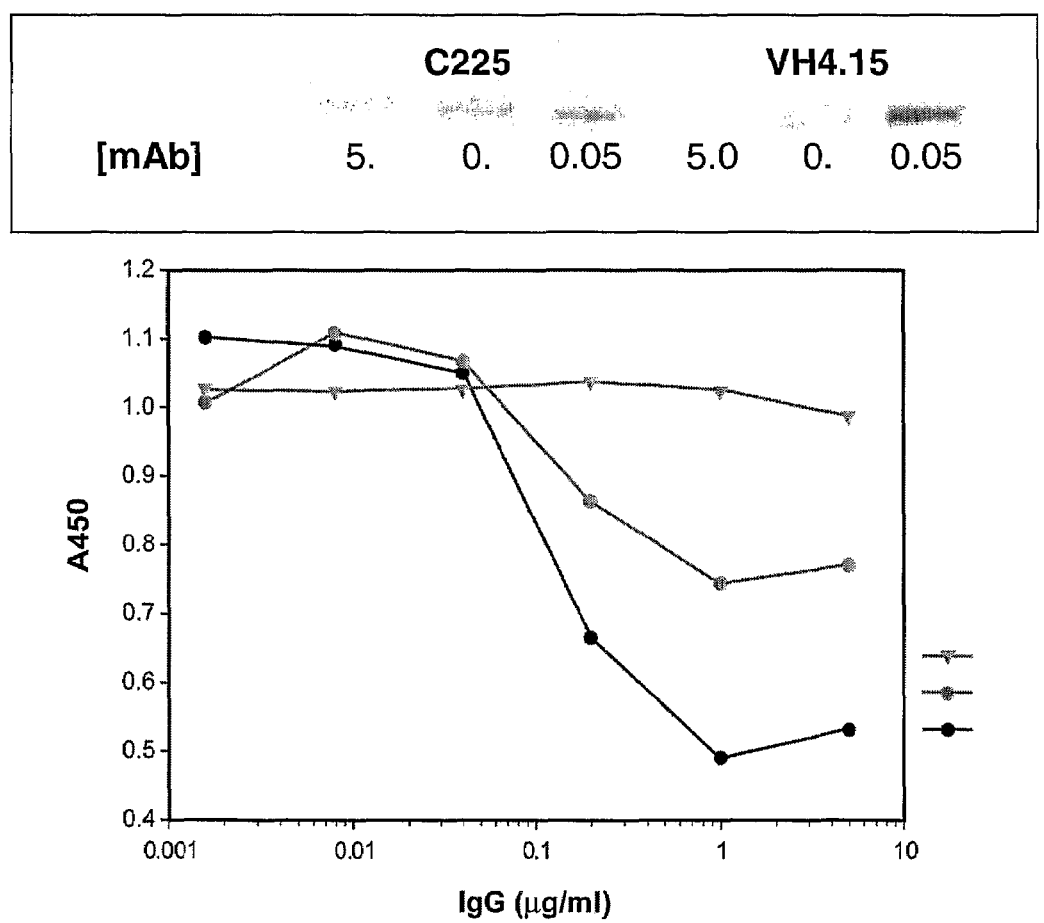
FIG. 5. shows that inhibition of A431 cell proliferation by antibody 4.15 and chimeric antibody C225 correlates to inhibition of EGFR phosphorylation.

The results of phosphorylation of EGFR in the presence of monoclonal antibodies C225, VH4.15 and VH4.21 are shown in FIG. 4. As shown in FIG. 5, inhibition of phosphorylation correlated with antibody potency in a cell based assay in a comparison of monoclonal antibodies C224 and VH4.15.

Example 9

Anti-EGFR Antibody Induced Apoptosis

The ability of anti-EGFR antibodies to inhibit EGFR activation is assayed by induction of apoptosis of A431 cells as follows. A431 cells at 20000 cells/well in 24-well plates are incubated with 1.0 ug/mL of antibody for 0, 3, 7, 24 or 48 hours. Apoptosis is measured by ELISA for DNA fragmentation (Roche). Baseline apoptosis from a non-specific antibody is subtracted from the mean.

Figure 6:
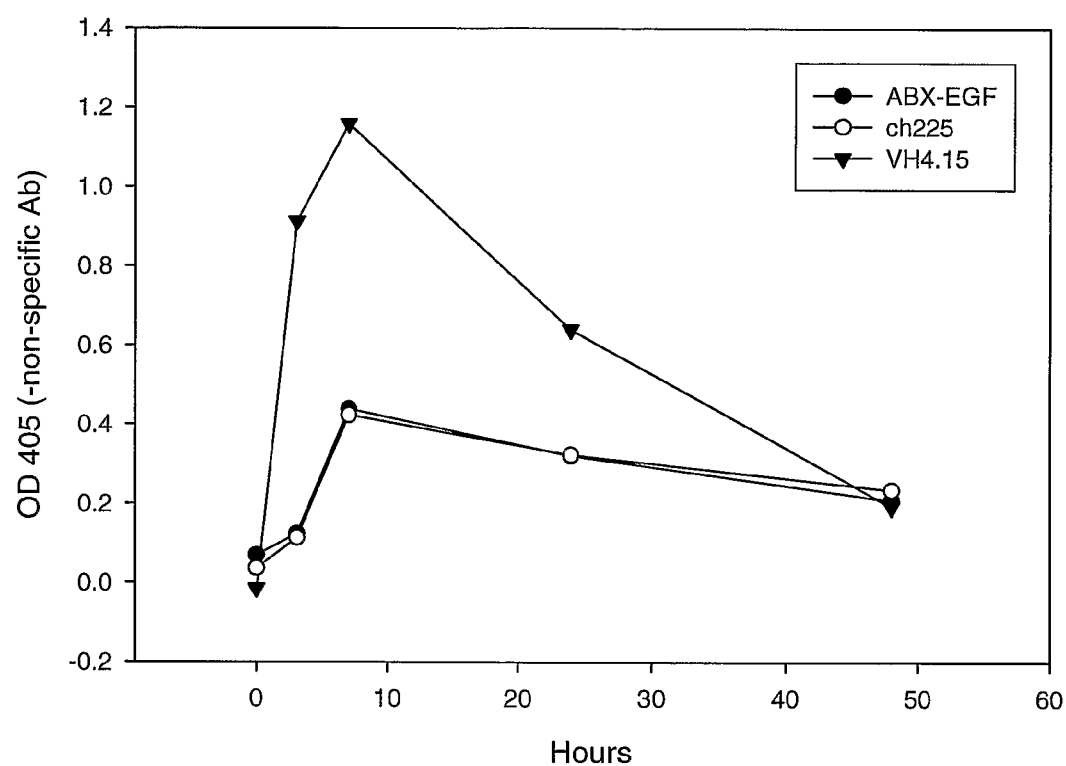
FIG. 6. shows the results of an assay for antibody induction of apoptosis of A431 cells by full-length antibodies 4.15, chimeric antibody C225, and human antibody ABX-EGF.

Results of anti-EGFR induced apoptosis of A431 cells by full length monoclonal antibodies C225, ABX-EGF, and VH4.15 are shown in FIG. 6.

Example 10

Treatment of A431 Tumors in a Mouse Model with Anti-EGFR Antibodies

The ability of anti-EGFR antibodies to inhibit activation of EGFR in vivo was examined with multiple dosages of antibodies in a mouse model having established A431 tumors. This mouse tumor model assay is carried out as follows. On day 0, growing, cultured A431 cells are obtained, counted, and resuspended to a concentration of $5 \times 10^7$. 7 week old male CB17-SCID mice (Taconic) are injected subcutaneously with 10⁷ cells (i.e. 200 µl) into the left flank (EC). Once tumors measure ~300 mm³ (typically at about 21 days), animals are injected intraperitoneally with 0.5 mg antibody/mouse in a volume of approximately 250-300 µl twice weekly (Tues/Fri), with control animals receiving 250 µl saline. A total of 5 antibody injections are given. Tumor volume is measured three times weekly for a total of three weeks starting with the first administration of antibody.

Figure 7:
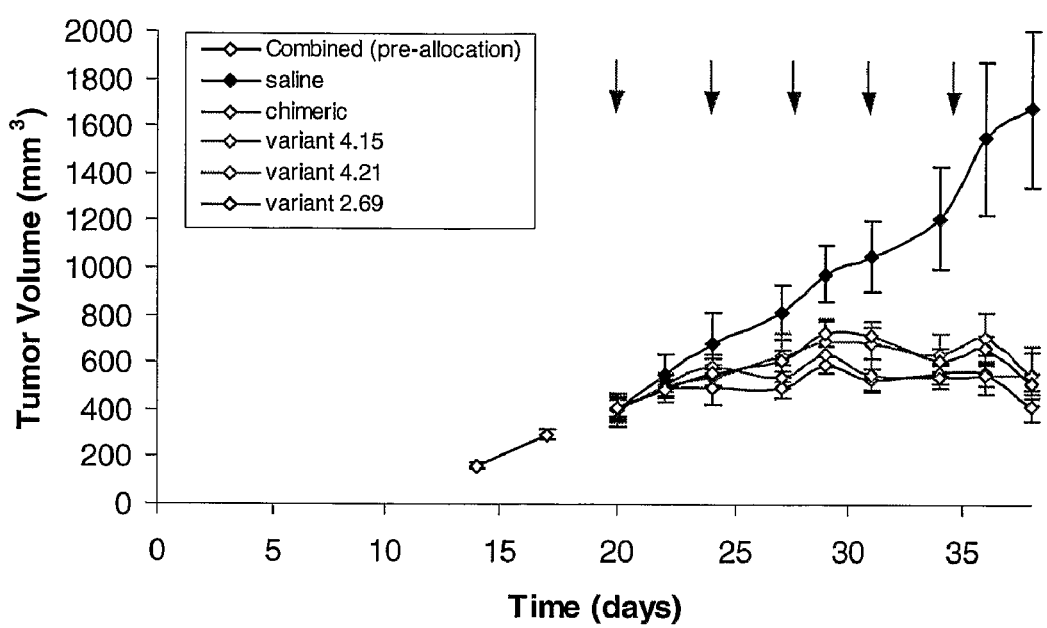
FIG. 7. shows the inhibition of A431 tumors in a mouse model by full-length antibodies 2.69, 4.15, 4.21, and chimeric antibody C225.

Results of a treatment of A431 tumors in a mouse model with anti-EGFR antibodies is shown in FIG. 7.

We claim:

1. An isolated EGFR antibody, or antigen binding portion thereof, comprising a heavy chain variable region (HCVR) and a light chain variable region (LCVR), wherein said HCVR and said LCVR are selected from the group consisting of:
   a) a HCVR having the amino acid sequence shown in SEQ ID NO: 49 and a LCVR having the amino acid sequence shown in SEQ ID NO:66;
   b) a HCVR having the amino acid sequence shown in SEQ ID NO: 51 and a LCVR having the amino acid sequence shown in SEQ ID NO: 68;
   c) a HCVR having the amino acid sequence shown in SEQ ID NO: 55 and a LCVR having the amino acid sequence shown in SEQ ID NO: 72; and
   d) a HCVR having the amino acid sequence shown in SEQ ID NO: 56 and a LCVR having the amino acid sequence shown in SEQ ID NO: 73.

2. The antibody of claim 1, wherein said antibody is a full-length antibody, a substantially intact antibody, a Fab fragment, a F(ab')$_2$ fragment, or a single chain Fv fragment.

3. A pharmaceutical composition comprising said antibody of claim 1 and a pharmaceutically acceptable carrier.

4. A method of treating an EGFR mediated cancer in a patient in need thereof comprising administering to said patient an effective amount of the antibody of claim 1.

* * * * *